United States Patent
Hausheer

(10) Patent No.: US 10,413,538 B2
(45) Date of Patent: Sep. 17, 2019

(54) ADMINISTRATION OF KARENITECIN FOR THE TREATMENT OF PLATINUM AND/OR TAXANE CHEMOTHERAPY-RESISTANT OR -REFRACTORY ADVANCED OVARIAN CANCER

(71) Applicant: BioNumerik Pharmaceuticals, Inc., San Antonio, TX (US)

(72) Inventor: Frederick H Hausheer, Fair Oaks Ranch, TX (US)

(73) Assignee: BioNumerik Pharmaceuticals, Inc., San Antonio ( * ) Notice: Subject to any disclaimer, the term of this patent is extended or adjusted under 35 U.S.C. 154(b) by 0 days.

(21) Appl. No.: 14/267,333

(22) Filed: May 1, 2014

(65) Prior Publication Data

US 2014/0336150 A1 Nov. 13, 2014

Related U.S. Application Data

(60) Provisional application No. 61/855,094, filed on May 8, 2013.

(51) Int. Cl.
*A61K 31/4745* (2006.01)

(52) U.S. Cl.
CPC ................ *A61K 31/4745* (2013.01)

(58) Field of Classification Search
CPC ................................. A61K 31/4745
See application file for complete search history.

(56) References Cited

PUBLICATIONS

Sugiyama et al. (Oncology, Supplement, May 2003).*
Kavanagh et al. (Int. J. Gynecol. Cancer, 2008,18, 460-464).*
Sugiyama et al. Irinotecan (CPT-11) combined with cisplatin in patients with refractory or recurrent ovarian cancer. Cancer Letters, 128, 1998, 211-218.*
https://clinicaltrials.gov/ct2/show/NCT00054119 (2009).*
Pignata et al. (BMC Cancer (2008)8(252) 7pages.*
Kollmannsberger et al. (Oncology. 1999;56(1):1-12.).*
Daud et al. (Clin Cancer Res 2009;2479 15(7) 2479-2487).*
Clarke-Pearson et al. (J Clin Oncol (2001).*
ClinicalTrials.gov NCT00477282 2007.*

* cited by examiner

*Primary Examiner* — Shirley V Gembeh
(74) *Attorney, Agent, or Firm* — Scott A. Whitaker

(57) ABSTRACT

The present invention discloses and claims methods and compositions for the treatment of subjects having advanced ovarian cancer, including platinum and/or taxane chemotherapy resistant or refractory sub-populations, with the administration to the subject having advanced ovarian cancer of the silicon-containing highly lipophilic camptothecin derivative (HLCD), Karenitecin (also known as BNP1350; cositecan; 7-[(2'-trimethylsilyl)ethyl]-20(S) camptothecin) in an amount sufficient to provide a therapeutic benefit. The administration of Karenitecin by intravenous (i.v.) and/or oral methodologies are also disclosed and claimed. Methods for the administration of Karenitecin to increase Progression Free Survival (PFS) are also disclosed and claimed herein.

7 Claims, 1 Drawing Sheet

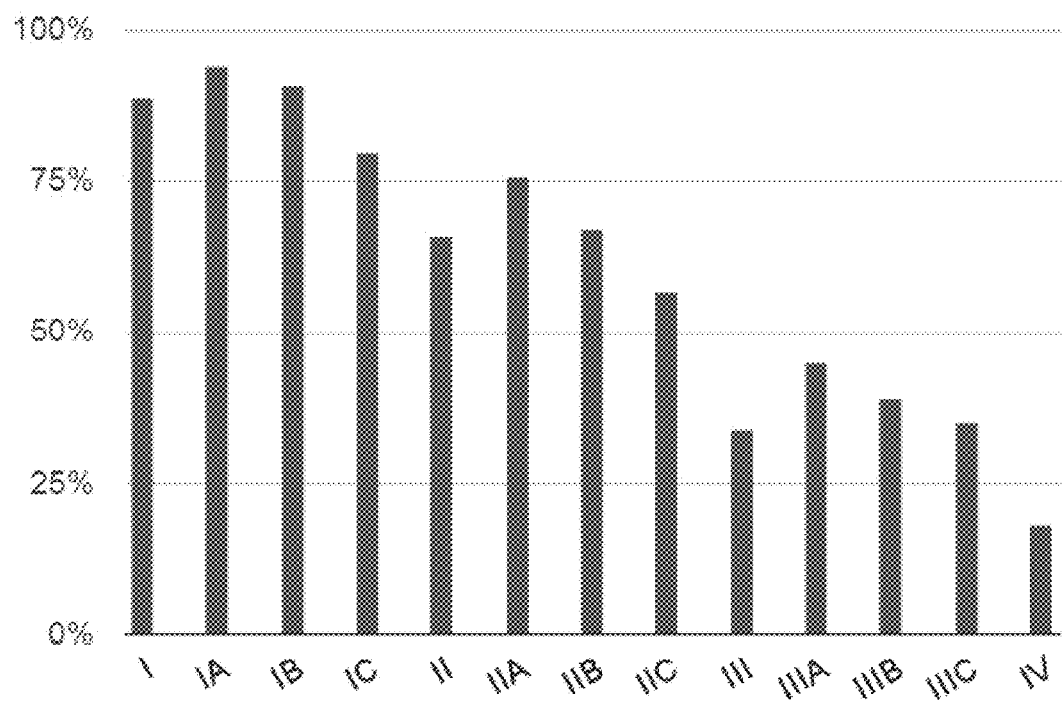

ADMINISTRATION OF KARENITECIN FOR THE TREATMENT OF PLATINUM AND/OR TAXANE CHEMOTHERAPY-RESISTANT OR -REFRACTORY ADVANCED OVARIAN CANCER

RELATED APPLICATIONS

The present application claims priority to U.S. Provisional Patent Application Ser. No. 61/855,094, with a filing date of May 8, 2013, and entitled: "ADMINISTRATION OF KARENITECIN FOR THE TREATMENT OF PLATINUM AND TAXANE CHEMOTHERAPY-RESISTANT OR -REFRACTORY ADVANCED OVARIAN CANCER", the disclosure of which is herein incorporated by reference in its entirety.

FIELD OF THE INVENTION

The present invention relates to the use of camptothecin derivatives as anti-cancer drugs. More specifically, the present invention is related to the use of the silicon-containing highly lipophilic camptothecin derivative (HLCD), Karenitecin, for the treatment of subjects with advanced ovarian cancer, including platinum and/or taxane chemotherapy-resistant or -refractory advanced ovarian cancer subjects.

BACKGROUND OF THE INVENTION

In brief, the present invention discloses methods and compositions for the treatment of platinum and/or taxane chemotherapy-resistant or -refractory advanced ovarian cancer subjects by i.v. and/or oral administration of the silicon-containing highly lipophilic camptothecin derivative (HLCD), Karenitecin (also known as BNP1350; cositecan; 7-[(2'-trimethylsilyl)ethyl]-20(S) camptothecin).

I. Ovarian Cancer

It is estimated that gynecological malignancies account for approximately 18.6% of all new cancer cases diagnosed and approximately 15.3% of all cancer related deaths in women worldwide. Of the gynecological malignancies, ovarian carcinoma is the second most common malignancy after cervical cancer. In 2002, ovarian cancer accounted for 204,200 new cases and 124,700 deaths representing approximately 4.0% of new cancer cases and 4.2% of cancer related deaths in women. See, e.g., Modugno F. Ovarian cancer and polymorphisms in the androgen and progesterone receptor genes. *Am. J. Epidemiol.* 159(4):319-335 (2004).

In the United States, it is estimated that each year there will be at least approximately 22,400 new cases diagnosed and 15,300 deaths due to ovarian carcinoma, accounting for approximately 3.0% of all cancers in women and causing more deaths than any other cancer of the female reproductive system. See, e.g., American Cancer Society: Cancer Facts and Figures 2009. Atlanta, Ga. American Cancer Society 2009. Unfortunately, as ovarian carcinoma is generally asymptomatic and not uncommonly clinically presents in protean diagnostic dilemmas by poorly defined, non-specific symptoms; the majority of patients are diagnosed with advanced stage disease of this cancer. Although much research has been conducted over the past several decades, the outcome for patients with advanced stage ovarian cancer still remains poor, with a 5-year survival rate ranging from less than 10% to 35% for women with stage III or IV disease.

Ovarian cancer is a cancerous growth arising from the ovary. Symptoms are frequently very subtle and non-specific, early on and even in later stages and may include: bloating, pelvic pain, frequent urination, and are easily confused with other illnesses. The three major histologic subtypes of ovarian carcinoma, based on pathologic and clinical features, include epithelial tumors, germ cell tumors, and sex cord-stromal tumors. The majority of ovarian cancers are epithelial in origin, accounting for 80% to 90% of ovarian malignancies. See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of Oncology*. 9th ed. Philadelphia, Pa.: Lippincott Williams & Wilkins; 2011:1368-1391. The epithelial tumors arise from the surface epithelium or serosa of the ovary. In the majority of cases, malignant epithelial ovarian tumors disseminate throughout the peritoneal cavity after exfoliation of malignant cells from the surface of the ovary. Tumor spread also occurs via the lymphatics from the ovary, and spread to lymph nodes is common.

Ovarian cancer is a surgically-staged cancer that is staged using the International Federation of Gynecology and Obstetrics (FIGO) staging system for cancer of the ovary. See, Benedet J L, Pecorelli S, Ngan H Y S, Hacker N F. *The FIGO Committee on Gynecologic Oncology. Staging Classifications and Clinical Practice Guidelines of Gynaecological Cancers*. 3rd ed. Elsevier; 2006:95-121. Tumors confined to the ovaries are classified as stage I. A tumor which involves one or both ovaries with pelvic extension is classified as stage II. A tumor which involves one or both ovaries with microscopically-confirmed peritoneal metastases outside the pelvis and/or regional lymph nodes metastasis is classified as stage III. Distant metastasis beyond the peritoneal cavity is classified as stage IV. Liver capsule metastasis is considered stage III, and liver parenchymal metastasis is considered stage IV.

II. Pharmacology of Platinum Compounds

The anti-neoplastic drug cisplatin (cis-diamminedichloroplatinum or "CDDP"), and related platinum based drugs including carboplatin and oxaliplatin, are widely used in the treatment of a variety of malignancies including, but not limited to, cancers of the ovary, lung, colon, bladder, germ cell tumors and head and neck. Platinum complexes are reported to act, in part, by aquation (i.e., to form reactive aqua species), some of which may predominate intracellularly, and subsequently form DNA intra-strand coordination chelation cross-links with purine bases, thereby cross-linking DNA, thereby interfering with its function. The currently accepted paradigm with respect to cisplatin's mechanism of action is that the drug induces its cytotoxic properties by forming a reactive monoaquo species that reacts with the exposed DNA major groove N7 nitrogen contained within the imidazole components of guanine and adenosine found in nuclear DNA to form intrastrand platinum-DNA adducts. However, the exact mechanism of action of cisplatin is not completely understood and remains a subject of continued research interest within the scientific community. Thus, this mechanism is believed to work predominantly through DNA intra-strand cross-links, and less commonly, through interstrand cross-links, thereby disrupting the DNA structure and function, which is cytotoxic to cancer cells. Platinum-resistant cancer cells are resilient to the cytotoxic actions of these agents. Certain cancers exhibit intrinsic de novo natural resistance to the killing effects of platinum agents and undergo no apoptosis, necrosis or regression following initial platinum compound treatment. In contrast, other types of cancers exhibit cytotoxic sensitivity to platinum drugs, as evidenced by tumor regression following initial treatment, but subsequently develop an increasing level of platinum resistance, which is manifested as a reduced responsiveness and/or tumor growth following treatment with the platinum drug (i.e., "acquired resistance"). Accordingly, new chemotherapeutic agents are continually being sought which will effectively kill tumor cells, but that are also insensitive or less susceptible to tumor-mediated drug resistance mechanisms that are observed with other platinum agents.

The reaction for cisplatin hydrolysis is illustrated below in Scheme I:

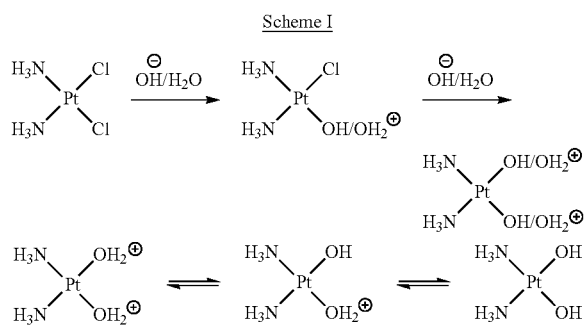

In neutral pH (i.e., pH 7), deionized water, cisplatin hydrolyzes to monoaquo/monohydroxy platinum complexes, which is less likely to further hydrolyze to diaqua complexes. However, cisplatin can readily form monoaquo and diaqua complexes by precipitation of chloro ligand with inorganic salts (e.g., silver nitrate, and the like). Also, the chloro ligands can be replaced by existing nucleophile (e.g., nitrogen and sulfur electron donors, etc.) without undergoing aquation intermediates.

Cisplatin is relatively stable in human plasma, where a high concentration of chloride prevents aquation of cisplatin. However, once cisplatin enters a tumor cell, where a much lower concentration of chloride exists, one or both of the chloro ligands of cisplatin is displaced by water to form an aqua-active intermediate form (as shown above), which in turn can react rapidly with DNA purines (i.e., Adenine and Guanine) to form stable platinum-purine-DNA adducts.

Cisplatin enters the cell through both passive diffusion and by active transport. The pharmacological behavior of cisplatin is in part determined by hydrolysis reactions that occur once cisplatin is inside the cell where the chloride concentration is essentially zero in nearly all major body organs, including the ovary. In this intracellular milieu, one chlorine ligand is replaced by a water molecule to yield an aquated version of cisplatin. The aquated platinum can then react with a variety of intracellular nucleophiles. Cisplatin binds to RNA more extensively than to DNA and to DNA more extensively than to protein; however, all of these reactions are thought to occur intracellularly. Thus, upon administration, a chloride ligand undergoes slow displacement with water (an aqua ligand) molecules, in a process termed aquation. The aqua ligand in the resulting $[PtCl(H_2O)(NH_3)_2]^+$ is easily displaced, allowing cisplatin to coordinate a basic site in DNA. Subsequently, the platinum cross-links two bases via displacement of the other chloride ligand. Cisplatin crosslinks DNA in several different ways, interfering with cell division by mitosis, as well as by DNA transcription and replication. The damaged DNA elicits various DNA repair mechanisms, which in turn activate apoptosis when repair proves impossible. Most notable among the DNA changes are the 1,2-intrastrand cross-links with purine bases. These include 1,2-intrastrand d(GpG) adducts which form nearly 90% of the platinum adducts and the less common 1,2-intrastrand d(ApG) adducts. 1,3-intrastrand d(GpXpG) adducts may also occur, but are readily excised by the nucleotide excision repair (NER) mechanism. Other adducts include inter-strand crosslinks and nonfunctional adducts that have been postulated to contribute to cisplatin's activity. In some cases, replicative bypass of the platinum 1,2-d(GpG) crosslink can occur allowing the cell to faithfully replicate its DNA in the presence of the platinum cross link, but often if this 1,2-intrastrand d(GpG) crosslink is not repaired, it interferes with DNA replication ultimately resulting in apoptosis.

The formation of cisplatin-DNA adducts that interfere with DNA replication is illustrated in Scheme II:

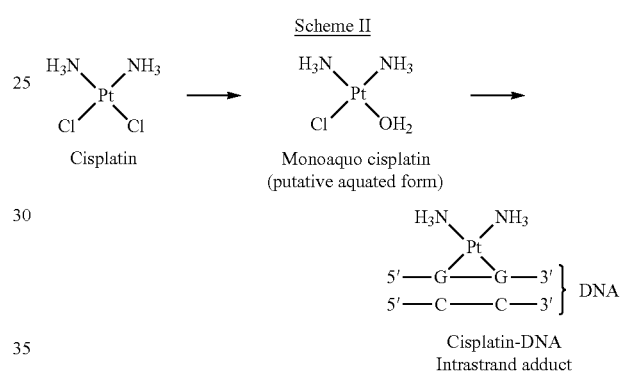

Interaction with cellular proteins, particularly High Mobility Group (HMG) chromosomal domain proteins (which are involved with transcription, replication, recombination, and DNA repair), has also been advanced as a mechanism of interfering with mitosis, although this is probably not its primary method of action. It should also be noted that although cisplatin is frequently designated as an alkylating agent, it has no alkyl group and cannot carry out alkylating reactions. Accordingly, it is more accurately classified as an alkylating-like agent.

III. Pharmacology of Taxanes

Taxanes are semi-synthetically derived analogues of naturally occurring compounds derived from plants. In particular, taxanes are derived from the needles and twigs of the European yew (*Taxus baccata*), or the bark of the Pacific yew (*Taxus brevifolia*). The most widely known taxanes at this time are paclitaxel (Taxol and Abraxane) and docetaxel (Taxotere), which are widely utilized as antineoplastic agents.

Paclitaxel was discovered in the late 1970s, and was found to be an effective antineoplastic agent with a mechanism of action different from then-existing chemotherapeutic agents. Taxanes are recognized as effective agents in the treatment of many solid tumors which are refractory to other antineoplastic agents.

Paclitaxel has the molecular structure shown below as Formula (A):

(A)

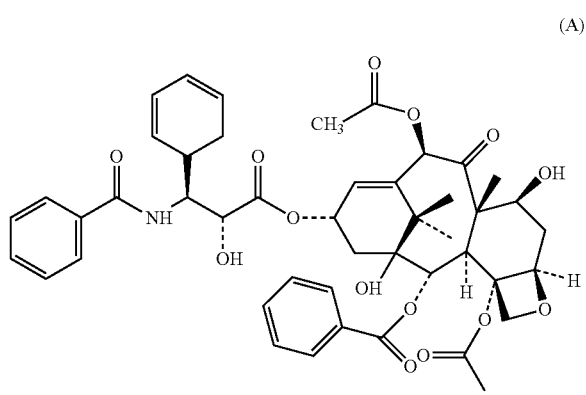

Docetaxel is an analog of Paclitaxel, and has the molecular structure shown below as Formula (B):

(B)

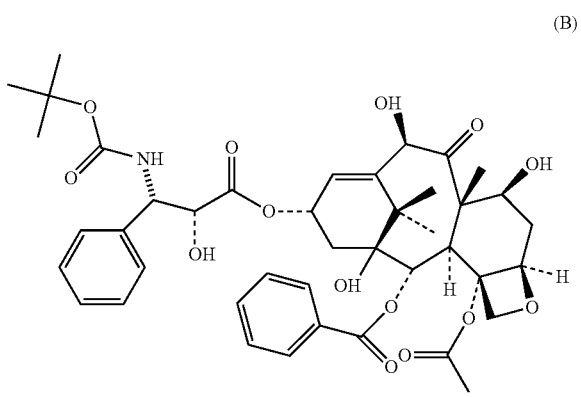

Taxanes exert their biological effects on the cell microtubules and act to promote the polymerization of tubulin, a protein subunit of spindle microtubules. The end result is the inhibition of depolymerization of the microtubules, which causes the formation of stable and nonfunctional microtubules. This disrupts the dynamic equilibrium within the microtubule system, and arrests the cell cycle in the late $G_2$ and M phases, which inhibits cell replication. Taxanes interfere with the normal function of microtubule growth and arrest the function of microtubules by hyper-stabilizing their structure. This destroys the cell's ability to use its cytoskeleton in a flexible manner.

Taxanes function as an anti-neoplastic agent by binding to the N-terminal 31 amino acid residues of the β-tubulin subunit in tubulin oligomers or polymers, rather than tubulin dimers. Unlike other anti-microtubule agents (e.g., vinca alkaloids) which prevent microtubule assembly, submicromolar concentrations of taxanes function to decrease the lag-time and shift the dynamic equilibrium between tubulin dimers and microtubules (i.e., the hyperpolymerization of tubulin oligomers) toward microtubules assembly and stabilize the newly formed microtubules against depolymerization. The microtubules which are formed are highly stable, thereby inhibiting the dynamic reorganization of the microtubule network. See, e.g., Rowinsky, E. K., et al., Taxol: The prototypic taxane, an important new class of antitumor agents. *Semin. Oncol.* 19:646 (1992). Tubulin is the "building block" of microtubules, the resulting microtubule/taxane complex does not have the ability to disassemble. Thus, the binding of taxanes inhibit the dynamic reorganization of the microtubule network. This adversely affects cell function because the shortening and lengthening of microtubules (i.e., dynamic instability) is necessary for their function as a mechanism to transport other cellular components. For example, during mitosis, microtubules position the chromosomes during their replication and subsequent separation into the two daughter-cell nuclei.

In addition, even at submicromolar concentrations, the taxanes also induce microtubule bundling in cells, as well as the formation of numerous abnormal mitotic asters (which unlike mitotic asters formed under normal physiological conditions, do not require centrioles for enucleation. Thus, the taxanes function to inhibit the proliferation of cells by inducing a sustained mitotic "block" at the metaphase-anaphase boundary at a much lower concentration than that required to increase microtubule polymer mass and microtubule bundle formation. See, e.g., Rao, S., et al., Direct photoaffinity labeling of tubulin with taxol. *J. Natl. Cancer Inst.* 84:785 (1992). It should be noted that many of the deleterious side-effects caused by the taxanes are due to the sustained mitotic "block" at the metaphase-anaphase boundary in normal (i.e., non-neoplastic cells).

In addition to stabilizing microtubules, the taxane, paclitaxel, may act as a "molecular sponge" by sequestering free tubulin, thus effectively depleting the cells supply of tubulin monomers and/or dimers. This activity may trigger the aforementioned apoptosis. One common characteristic of most cancer cells is their rapid rate of cell division. In order to accommodate this, the cytoskeleton of the cancer cell undergoes extensive restructuring. Paclitaxel is an effective treatment for aggressive cancers because it adversely affects the process of cell division by preventing this restructuring. Although non-cancerous cells are also adversely affected, the rapid division rate of cancer cells make them far more susceptible to paclitaxel treatment.

Further research has also indicated that paclitaxel induces programmed cell death (apoptosis) in cancer cells by binding to an apoptosis stopping protein called B-cell leukemia 2 (Bcl-2), thus arresting its function.

The molecular structure of taxanes are complex alkaloid esters consisting of a taxane system linked to a four-member oxetan ring at positions C-4 and C-5. The taxane rings of both paclitaxel and docetaxel, but not 10-deacetylbaccatin III, are linked to an ester at the C-13 position. Experimental and clinical studies have demonstrated that analogs lacking the aforementioned linkage have very little activity against mammalian tubulin. Moreover, the moieties at C-2' and C-3' are critical with respect to its full biological activity, specifically, for the anti-microtubule hyperpolymerization effect of taxane. The C-2' —OH is of paramount importance for the activity of taxol and while the C-2' —OH of taxol can be "substituted" by a sufficiently strong nucleophile (see, PCT/US98/21814; page 62, line 8-27) the biological activity would be greatly diminished. See, e.g., Lataste, H., et al., Relationship between the structures of Taxol and baccatine III derivatives and their in vitro action of the disassembly of mammalian brain. *Proc. Natl. Acad. Sci.* 81:4090 (1984). For example, it has been demonstrated that the substitution of an acetyl group at the C-2' position markedly reduces taxane activity. See, e.g., Gueritte-Voegelein, F., et al., Relationships between the structures of taxol analogues and their antimitotic activity. *J. Med. Chem.* 34:992 (1991).

Taxanes are toxic compounds having a low therapeutic index which have been shown to cause a number of different toxic effects in patients. The most well-known and severe adverse effects of taxanes are neurotoxicity and hematologic toxicity, particularly anemia and severe neutropenia/thrombocytopenia. Additionally, taxanes also cause hypersensitivity reactions in a large percentage of patients; gastrointestinal effects (e.g., nausea, diarrhea and vomiting); alopecia; anemia; and various other deleterious physiological effects, even at the recommended dosages. These Taxane medicaments include, in a non-limiting manner, docetaxel or paclitaxel (including the commercially-available paclitaxel derivatives Taxol and Abraxane), polyglutamylated forms of paclitaxel (e.g., Xyotax), liposomal paclitaxel (e.g., Tocosol), and analogs and derivatives thereof.

SUMMARY OF THE INVENTION

The present invention described and claimed herein has many attributes and embodiments including, but not limited to, those set forth or described or referenced in this Summary section. However, it should be noted that this Summary is not intended to be all-inclusive, nor is the invention described and claimed herein limited to, or by, the features or embodiments identified in said Summary. Moreover, this Summary is included for purposes of illustration only, and not restriction.

The present patent application discloses and claims new and novel inventions which have been derived from the results of a multi-center, multi-national, randomized, open-label, active-controlled, Phase III human clinical study to compare and evaluate the safety and efficacy of the silicon-containing highly lipophilic camptothecin derivative (HLCD) chemotherapeutic drug Karenitecin (also known as BNP1350; cositecan; 7-[(2'-trimethylsilyl)ethyl]-20(S) camptothecin) with that of the camptothecin-analogue chemotherapeutic drug Topotecan; wherein the drugs were administered to the trial subjects as a single, daily intravenous dose of either Karenitecin or Topotecan—[Karenitecin 1.0 mg/m$^2$/day×5 (first 5 consecutive days per cycle) in a 60 minute I.V. infusion or Topotecan 1.5 mg/m$^2$/day×5 (first 5 consecutive days per cycle) in a 30 minute I.V. infusion] every 21 days in patients with stage III/IV advanced epithelial ovarian cancer who are resistant or refractory to platinum- and taxane-based chemotherapy regimens, as indicated by relapse/progression while currently on, or within 6 months of completion of, platinum/taxane treatment in a first-line or second-line setting. In addition, patients with a best response of Stable Disease ("SD") after at least 6 cycles of platinum/taxane treatment in the first-line setting were considered platinum-resistant for purposes of the instant Phase III clinical trial.

All patients admitted to this Phase III clinical trial were documented to be platinum- and/or taxane-refractory or resistant and have incurable disease. All patients admitted to the clinical study must have had their disease progress while receiving chemotherapeutic treatment or within 6 months of first or second line platinum- or taxane-based treatment. It is important to note that, currently, there is no FDA-approved chemotherapeutic drug for this specific aforementioned indication.

The Primary Endpoint of the disclosed Phase III clinical study was Progression Free Survival ("PFS"); which was defined as the time period from the date of randomization to the date of first radiographically documented Progressive Disease ("PD") or date of death due to any cause, taking either event date that occurred first. The date of PD was determined by radiographical objective disease (RECIST) measurement method. The Secondary Endpoints of the disclosed Phase III clinical study included: (i) Overall Survival (hereinafter "OS"), defined as the time from the date of randomization to the date of death due to any cause; (ii) Incidence of anemia, defined as the proportion of patients who experience ≥grade 3 anemia based on National Cancer Institute Common Terminology Criteria for Adverse Events (NCI-CTCAE) criteria at any time post-baseline after receiving study treatment; (iii) Incidence of neutropenia (including febrile neutropenia), defined as the proportion of patients who experience ≥grade 3 neutropenia based on NCI-CTCAE criteria at any time post-baseline after receiving study treatment; and (iv) Incidence of thrombocytopenia, defined as the proportion of patients who experience ≥grade 3 thrombocytopenia based on NCI-CTCAE criteria at any time post-baseline after receiving study treatment.

Until the results of the instant Phase III clinical trial became known, the probability for cure for patients with advanced ovarian cancer had previously been thought to be remote (with palliation and optimizing the quality of life being the primary treatment goals). The unexpected observations in the instant trial regarding the ability of the subjects receiving Karenitecin to tolerate both the full treatment cycle regimen with reduced adverse effects and a greater number of total chemotherapeutic cycles may improve the probability of advanced ovarian cancer being able to be treated as a chronic disease or even for a cure.

BRIEF DESCRIPTION OF THE FIGURES

FIG. 1: illustrates, in bar graph form, the relative five (5) year survival of patients with Stage I to Stage IV invasive epithelial ovarian cancer.

DETAILED DESCRIPTION OF THE INVENTION

The descriptions and embodiments set forth herein are not intended to be exhaustive, nor do they limit the present invention to the precise forms disclosed. They are included to illustrate the principles of the invention, and its application and practical use by those skilled in the art.

In addition, included is a listing of some of the terms used herein. However, it should be noted that this listing of terms is provided solely as guidance for the reader. Unless otherwise explained, all technical and scientific terms used herein have the same meaning as commonly understood by one of ordinary skill in the art to which this disclosure belongs. All publications, patent applications, patents, and other references mentioned herein are incorporated by reference in their entirety. In case of conflict, the present Specification, including explanations of terms, will control. In addition, the materials, methods, and examples are for illustrative purposes only, and are not intended to be limiting.

Listing of Terms Utilized in Present Patent Application

As utilized herein, the term "adenocarcinoma" refers to a cancer that originates in glandular tissue. Glandular tissue comprises organs that synthesize a substance for release such as hormones. Glands can be divided into two general groups: (i) endocrine glands—glands that secrete their product directly onto a surface rather than through a duct, often into the blood stream and (ii) exocrine glands—glands that secrete their products via a duct, often into cavities inside the body or its outer surface. However, it should be noted that to be classified as adenocarcinoma, the tissues or cells do not necessarily need to be part of a gland, as long as they have secretory properties. Adenocarcinoma may be derived from various tissues including, but not limited to, breast, colon, lung, prostate, salivary gland, stomach, liver, gall bladder, pancreas (99% of pancreatic cancers are ductal adenocarcinomas), ovary, cervix, vagina, and uterus, as well as unknown primary adenocarcinomas. Adenocarcinoma is a neoplasm which frequently presents marked difficulty in differentiating from where and from which type of glandular tissue the tumor(s) arose. Thus, an adenocarcinoma identified in the lung may have had its origins (or may have metastasized) from an ovarian adenocarcinoma. Cancer for which a primary site cannot be found is called cancer of unknown primary.

As utilized herein, the medical definitions for the terms "adverse effect", "adverse event", "adverse experience", "adverse reaction", and "unexpected adverse reaction" have previously been agreed to by consensus of the more than thirty Collaborating Centers of the WHO International Drug Monitoring Centre (Uppsala, Sweden). See, Edwards, I. R., et al., Harmonisation in Pharmacovigilance *Drug Safety* 10(2):93-102 (1994). The following medical definitions, with input from the WHO Collaborative Centre, have been agreed to:

1. Adverse Event (Adverse Effect or Adverse Experience)—Any untoward medical occurrence in a patient or clinical investigation subject administered a pharmaceutical product and which does not necessarily have to have a causal relationship with this treatment. An Adverse Event (AE) can therefore be any unfavorable and unintended sign (including an abnormal laboratory finding, for example), symptom, or disease temporally associated with the use of a medicinal product, whether or not considered related to the medicinal product.

2. Adverse Drug Reaction (ADR)—In the pre-approval clinical experience with a new medicinal product or its new usages, particularly as the therapeutic dose(s) may not be established: all noxious and unintended responses to a medicinal product related to any dose should be considered adverse drug reactions. Drug-related Adverse Events are rated from grade 1 to grade 5 and relate to the severity or intensity of the event. Grade 1 is mild, grade 2 is moderate, grade 3 is severe, grade 4 is life threatening, and grade 5 results in death.

3. Unexpected Adverse Drug Reaction—An adverse reaction, the nature or severity of which is not consistent with the applicable product information.

Serious Adverse Event or Adverse Drug Reaction: A Serious Adverse Event (experience or reaction) is any untoward medical occurrence that at any dose:
(a) Results in death or is life-threatening. It should be noted that the term "life-threatening" in the definition of "serious" refers to an event in which the patient was at risk of death at the time of the event; it does not refer to an event which hypothetically might have caused death if it were more severe.
(b) Requires inpatient hospitalization or prolongation of existing hospitalization.
(c) Results in persistent or significant disability/incapacity, or
(d) Is a congenital anomaly/birth defect.

As utilized herein the term "cancer" refers to all known forms of cancer including, solid forms of histopathologically classified forms of cancer (e.g., those that form tumors), lymphomas, and non-solid tumors e.g., leukemias.

As used herein, an "effective amount" or a "pharmaceutically-effective amount" in reference to the compounds or compositions of the instant invention refers to the amount that is sufficient to induce a desired biological, pharmacological, or therapeutic outcome in a subject with neoplastic disease. That result can be reduction, prevention, mitigation, delay, shortening the time to resolution of, alleviation of the signs or symptoms of, or exert a medically-beneficial effect upon the underlying pathophysiology or pathogenesis of an expected or observed side-effect, toxicity, disorder or condition, or any other desired alteration of a biological system. In the present invention, the result will generally include the reduction, prevention, mitigation, delay in the onset of, attenuation of the severity of, and/or a hastening in the resolution of, or reversal of chemotherapy-associated toxicity; an increase in the frequency and/or number of treatments; an increase in duration of chemotherapeutic therapy; an increase or improvement in Progression Free Survival (PFS); and/or Complete Remission (CR).

The terms "Highly Lipophilic Camptothecin Derivatives (HLCDs or an HCLD)", as utilized herein, are defined as camptothecin analogs having a water solubility of less than 5 µg/mL of water.

As used herein the term "Quality of Life" or "QOL" refers, in a non-limiting manner, to a maintenance or increase in a cancer subject's overall physical and mental state (e.g., cognitive ability, ability to communicate and interact with others, decreased dependence upon analgesics for pain control, maintenance of ambulatory ability, maintenance of appetite and body weight (lack of cachexia), lack of or diminished feeling of "hopelessness"; continued interest in playing a role in their treatment, and other similar mental and physical states).

The term "platinum sensitivity" is defined herein as the disease-free or treatment-free interval in a subject having ovarian cancer, after the treatment of the subject with a platinum-based chemotherapy agent, including combination therapy involving a platinum-based agent. Platinum sensitivity has emerged as an important and significant predictive indicator of response to second-line chemotherapy.

As used herein, the term "refractory", refers to a subject who is suffering from an ovarian cancer which fails to respond reasonably in a favorable manner in terms of tumor shrinkage or duration of stabilization or shrinkage in response to treatment with a platinum and/or taxane chemotherapy agent(s) in the first line setting. Such patients have a best response of stable disease or their tumor(s) progress during such treatment and have a poor prognosis.

As used herein, the term "resistant", with respect to a platinum- and/or taxane-based chemotherapy agent, refers to a subject who is suffering from an ovarian cancer which fails to respond to treatment with a platinum and/or taxane chemotherapy agent(s) for a time of greater than 6 months or more, or whose tumor(s) progresses within 6 months of completion of treatment with a platinum and/or taxane chemotherapy agent(s).

The term "platinum-free interval" is defined herein as the time that elapses after the completion of the initial platinum-based therapy (including combination therapies involving the administration of platinum-based agents) in a subject having a relapse of ovarian cancer before further treatment of the subject with a platinum- and/or taxane-based chemotherapeutic agent occurs.

As used herein, the terms "chemotherapeutic agent" or "chemotherapy agent" or "chemotherapeutic drug" refer to an agent that reduces, prevents, mitigates, limits, and/or delays the growth of metastases or neoplasms, or kills neoplastic cells directly by necrosis or apoptosis of neoplasms or any other mechanism, or that can be otherwise used, in a pharmaceutically-effective amount, to reduce, prevent, mitigate, limit, and/or delay the growth of metastases or neoplasms in a subject with neoplastic disease.

Chemotherapeutic agents include, for example, fluoropyrimidines; pyrimidine nucleosides; purine nucleosides; antifolates, platinum agents; anthracyclines/anthracenediones; epipodophyllotoxins; camptothecins (e.g., Karenitecin); hormones; hormonal complexes; antihormonals; enzymes, proteins, peptides and polyclonal and/or monoclonal antibodies; immunological agents; vinca alkaloids; taxanes; epothilones; antimicrotubule agents; alkylating agents; antimetabolites; topoisomerase inhibitors; antivirals; and various other cytotoxic and cytostatic agents.

As utilized herein, the terms "chemotherapy", "chemotherapeutic regimen(s)", or "chemotherapy cycle" refer to treatment using the above-mentioned chemotherapeutic agents with or without the compounds of the present invention.

As utilized herein, the term "chemotherapeutic effect" refers to the ability of an agent to reduce, prevent, mitigate, limit, and/or delay the growth of metastases or neoplasms, or kill neoplastic cells directly by necrosis or apoptosis of neoplasms or any other mechanism, or that can be otherwise used to reduce, prevent, mitigate, limit, and/or delay the growth of metastases or neoplasms in a subject with neoplastic disease.

As utilized herein, the terms "cycle" or "chemotherapeutic cycle" refers to the administration of a complete regimen of medicaments to the patient in need thereof in a defined time period.

As used herein, the term "cytostatic agents" are mechanism-based agents that slow the progression of neoplastic disease and include drugs, biological agents, and radiation.

As used herein the term "cytotoxic agents" are any agents or processes that kill neoplastic cells and include drugs, biological agents, immunotherapy; and radiation. In addition, the term "cytotoxic" is inclusive of the term "cytostatic".

As used herein, the terms "platinum medicaments" or "platinum compounds" include all compounds, compositions, and formulations which contain a platinum ligand in the structure of the molecule. By way of non-limiting example, the valence of the platinum ligand contained therein may be platinum II or platinum IV. The platinum medicaments or platinum compounds disclosed in the present invention include, in a non-limiting manner, cisplatin, oxaliplatin, carboplatin, satraplatin, and analogs and derivatives thereof.

As used herein, the term "taxane medicaments" include, in a non-limiting manner, docetaxel or paclitaxel (including the commercially-available paclitaxel derivatives Taxol® and Abraxane®), polyglutamylated forms of paclitaxel (e.g., Xyotax®), liposomal paclitaxel (e.g., Tocosol®), and analogs and derivatives thereof.

As used herein, the terms "an amount sufficient to provide a therapeutic benefit", a "medically-sufficient dose", or a "medically-sufficient amount" in reference to the compounds or compositions of the instant invention refers to the dosage that is sufficient to induce a desired biological, pharmacological, or therapeutic outcome in a subject with neoplastic disease. That result can be: (i) cure or remission of previously observed cancer(s); (ii) shrinkage of tumor size; (iii) reduction in the number of tumors; (iv) delay or prevention in the growth or reappearance of cancer; (v) selectively sensitizing cancer cells to the anti-cancer activity of chemotherapeutic agents; (vi) restoring or increasing apoptotic effects or sensitivity in tumor cells; and/or (vii) increasing the time of survival of the patient, alone or while concurrently experiencing reduction, prevention, mitigation, delay, shortening the time to resolution of, alleviation of the signs or symptoms of the incidence or occurrence of an expected side-effect(s), toxicity, disorder or condition, or any other untoward alteration in the patient.

As utilized herein, the terms "Hazard Ratio", "HR", and "hazard ratio" refer to the chance of an event occurring with treatment "A" divided by the chance of the event occurring with treatment "B". The hazard ratio is an expression of the hazard or chance of events occurring in one treatment arm as a ratio of the hazard of the events occurring in the other treatment arm. A hazard ratio less than 1.0 means that treatment "A" is more favorable than treatment "B" in terms of the result being measured. As described herein for purposes of data references to hazard ratios, treatment "A" refers to treatment with Karenitecin and treatment "B" refers to treatment with Topotecan. Accordingly, a hazard ratio less than 1.0 relating to Karenitecin treatment refers to a more favorable outcome in the result being measured for Karenitecin treatment in comparison to the result being measured for the treatment other than Karenitecin. References to an "improvement" or "reduction" in the hazard ratio in favor of Karenitecin refer to a more favorable outcome in the result being measured for Karenitecin treatment in comparison to the result being measured for the treatment other than Karenitecin.

As used herein, the term "$mg/m^2$" represents the amount of a given compound or formulation in milligrams per square meter of the total body surface area of the subject to whom the compound or formulation is administered.

As used herein, the term "reducing" includes preventing and/or attenuating the overall severity of, delaying the initial onset of, and/or expediting the resolution of the acute and/or chronic pathophysiology associated with malignancy in a subject.

During the past 30 years, the camptothecins (CPTs), of which Karenitecin (also known as BNP1350; cositecan; 7-[(2'-trimethylsilyl)ethyl]-20(S) camptothecin) is a member, have emerged as an important new class of antitumor drugs. Currently, two water-soluble CPT derivatives have been approved by the United States Food and Drug Administration (FDA) for use in the treatment of patients with cancer. The first, Camptosar (irinotecan HCl, Pfizer, Inc; hereinafter referred to as "CPT-11"), is a water-soluble CPT analog that is indicated as a component of first-line therapy in combination with 5-fluorouracil and leucovorin for patients with metastatic carcinoma of the colon or rectum, and is also indicated for patients with metastatic carcinoma of the colon or rectum whose disease has recurred or progressed following initial fluorouracil-based therapy. See, Camptosar [package insert]. New York, N.Y.; Pfizer, Inc. (2006).

The second, Hycamtin (Topotecan HCl, GlaxoSmithKline; hereinafter referred to as "Topotecan"), is a water-soluble CPT analogue that is indicated for the treatment of metastatic carcinoma of the ovary after failure of initial or subsequent chemotherapy; small cell lung cancer sensitive disease after failure of first-line chemotherapy; and stage IV-B, recurrent, or persistent carcinoma of the cervix which is not amenable to curative treatment with surgery and/or radiation therapy. See, Hycamtin [package insert]. Research Triangle Park, NC: GlaxoSmithKline (2006).

The objective of the Phase III clinical study disclosed in the present patent application was to determine the safety and efficacy of intravenous Karenitecin versus Topotecan in patients with platinum and/or taxane-resistant or -refractory advanced ovarian cancer.

I. Ovarian Cancer

As previously discussed, it has been estimated that gynecological malignancies account for approximately 18.6% of all new cancer cases diagnosed and approximately 15.3% of all cancer related deaths in women worldwide. Of the gynecological malignancies, ovarian carcinoma is the second most common malignancy after cervical cancer. In 2002, ovarian cancer accounted for 204,200 new cases and 124,700 deaths representing approximately 4.0% of new cancer cases and 4.2% of cancer related deaths in women. See, e.g., Modugno F. Ovarian cancer and polymorphisms in the androgen and progesterone receptor genes. *Am. J. Epidemiol.* 159(4):319-335 (2004).

In the United States, it is estimated that each year there will be at least approximately 22,400 new cases diagnosed and 15,300 deaths due to ovarian carcinoma, accounting for approximately 3.0% of all cancers in women and causing more deaths than any other cancer of the female reproductive system. See, e.g., American Cancer Society: Cancer Facts and FIGS. 2009. Atlanta, Ga. American Cancer Society 2009. The lifelong risk of developing sporadic epithelial ovarian cancer is approximately 1.7%, although patients with a familial predisposition have a much higher lifetime risk, in the range of 10% to 40%. See, e.g., Jemal, A. et al., Cancer Statistics 2009. *CA Cancer J. Clin.* 59:225 (2009). The median age of diagnosis for sporadic disease is 60 years old, although patients with a genetic predisposition may develop this type of tumor earlier, often in their fifth decade. The age-specific incidence of sporadic disease increases with age, from 15-16 per 100,000 in the 40-to 44-year old age group to a peak rate of 57 per 100,000 in the 70- to 74-year old age group. See, Id.

Unfortunately, as ovarian carcinoma is generally asymptomatic; the majority of patients are diagnosed with advanced stage disease. Although much research has been conducted over the past several decades, the outcome for patients with advanced stage ovarian cancer still remains poor, with a 5-year survival rate ranging from less than 10% to 35% for women with stage III or IV disease.

Ovarian cancer is a cancerous growth arising from the ovary. Symptoms are frequently very subtle early on and may include: bloating, pelvic pain, frequent urination, and are easily confused with other illnesses. The 3 major histologic subtypes of ovarian carcinoma, based on pathologic and clinical features, include epithelial tumors, germ cell tumors, and sex cord-stromal tumors. The majority of ovarian cancers are epithelial in origin, accounting for 80% to 90% of ovarian malignancies. See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of Oncology.* 9th ed. Philadelphia, Pa.: Lippincott Williams & Wilkins; 2011:1368-1391. The epithelial tumors arise from the surface epithelium or serosa of the ovary. In the majority of cases, malignant epithelial ovarian tumors disseminate throughout the peritoneal cavity after exfoliation of malignant cells from the surface of the ovary. Tumor spread also occurs via the lymphatics from the ovary, and spread to lymph nodes is common.

Ovarian cancer is a surgically-staged cancer using the International Federation of Gynecology and Obstetrics (FIGO) staging system for cancer of the ovary and uses information obtained after surgery, which can include a total abdominal hysterectomy, removal of (usually) both ovaries and fallopian tubes, removal of (usually) the omentum, and pelvic (peritoneal) washing to assess any cytopathology therein. See, Benedet J L, Pecorelli S, Ngan H Y S, Hacker N F. *The FIGO Committee on Gynecologic Oncology. Staging Classifications and Clinical Practice Guidelines of Gynaecological Cancers.* 3rd ed. Elsevier; 2006:95-121. The ovaries contain the ova and secrete the hormones that control the reproductive cycle. Removing the ovaries and the fallopian tubes greatly reduces the amount of the hormones estrogen and progesterone circulating in the body. This can halt or slow breast and ovarian cancers that need these hormones to grow.

The general FIGO stages for ovarian cancer are set forth below:

Stage I—limited to one or both ovaries
    IA—involves one ovary; capsule intact; no tumor on ovarian surface; no malignant cells in ascites or peritoneal washings
    IB—involves both ovaries; capsule intact; no tumor on ovarian surface; negative washings
    IC—tumor limited to ovaries with any of the following: capsule ruptured, tumor on ovarian surface, positive washings Stage II—pelvic extension or implants
    IIA—extension or implants onto uterus or fallopian tube; negative washings
    IIB—extension or implants onto other pelvic structures; negative washings
    IIC—pelvic extension or implants with positive peritoneal washings Stage III—peritoneal implants outside of the pelvis; or limited to the pelvis with extension to the small bowel or omentum
    IIIA—microscopic peritoneal metastases beyond pelvis
    IIIB—macroscopic peritoneal metastases beyond pelvis <2 cm in size
    IIIC—peritoneal metastases beyond pelvis >2 cm or lymph node metastases Stage IV—distant metastases to the liver or outside the peritoneal cavity FIGO histopathologic classification of epithelial ovarian neoplasms includes:
(i) serous tumors; (ii) mucinous tumors; (iii) endometrioid tumors; (iv) clear cell tumors; (v) Brenner tumors; (vi) undifferentiated tumors (of epithelial structure, but are poorly-differentiated); and (vii) mixed epithelial tumors. Epithelial ovarian tumors are then further sub-classified by grading: (a) Gx—grade cannot be assessed; (b) G1—well differentiated; (c) G2—moderately differentiated; and (d) G3—poorly differentiated.

Generally, the prognoses of all ovarian tumors are independently affected by the following: (i) the specific stage of the cancer at time of diagnosis; (ii) the histological subtype and grading; and (iii) the volume of residual disease. Other important prognostic factors include performance status, platinum- or progression-free interval, and response of CA-125 to initial treatment. See, e.g., Benedet J L, Pecorelli S, Ngan H Y S, Hacker N F. *The FIGO Committee on Gynecologic Oncology. Staging Classifications and Clinical Practice Guidelines of Gynaecological Cancers.* 3rd ed. Elsevier; 2006:95-121. Epithelial carcinoma of the ovary is often described as a "silent killer" because the majority of patients do not present with symptoms until the disease has spread outside the ovary and pelvis (approximately 70% of patients with epithelial cancers of the ovary present with stage III or IV disease). See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of*

*Oncology. 9th ed.* Philadelphia, Pa.: Lippincott Williams & Wilkins; 2011:1368-1391. Patients with stage III disease have a 5-year survival rate of approximately 35%, which is dependent on the volume of disease in the upper abdomen. Patients with stage IV disease have a 5-year survival rate of less than 10%. After the administration of a post-operative platinum-based combination chemotherapy, 4-year survival rates for patients with optimal stage III disease (defined as only microscopic residual disease) is approximately 60%. See, Id. The relative five (5) year survival of patients with Stage I to Stage V invasive epithelial ovarian cancer is illustrated in FIG. 1.

In most cases, the exact cause of ovarian cancer remains unknown. Epithelial ovarian cancer is a clonal disease that arises from a single cell in more than 90% of cases. Multiple genetic changes must occur in the ovarian surface epithelium (OSE) to produce malignant transformation. Repeated rupture and repair (ovulation) of the OSE provides this opportunity for genetic aberrations. Hereditary factors are implicated in approximately 5-10% of all ovarian cancers. Thus far, the syndromes that have been identified are: (i) the Breast-Ovarian Cancer Syndrome, linked to an inherited mutation in the BRCA1 and the BRCA2 genes (this includes site specific Ovarian Cancer Syndrome); and (ii) Type II Lynch Syndrome, which also includes colon, breast, endometrial and prostate cancer in affected individuals. See, e.g., Lynch H T, Watson P, Lynch J F, Conway T A, Fili M. Hereditary ovarian cancer. Heterogeneity in age at onset. *Cancer* 71:(2 Suppl): 573-81 (1993); Struewing J P, Hartge P, Wacholder S, et al. The risk of cancer associated with specific mutations of BRCA1 and BRCA2 among Ashkenazi Jews. *N. Engl. J. Med.* 336:1401-1408 (1997). Several other molecular abnormalities have been identified in patients with epithelial ovarian cancer, although their contribution to malignant transformation is poorly understood. These abnormalities include: (i) deletions of 3p, 6q, 8p, and 10q; (ii) loss of heterozygosity is commonly observed on 11p, 13q, 16q, 17p, and 17q; (iii) mutations of the p53 oncogene occurs in over 50% of patients; (iv) amplification of HER2/neu gene is found in approximately 8% of patients and confers of poorer prognosis; and (v) expression of angiogenic cytokines such as vascular endothelial growth factor (VEGF) is frequently observed and confers a worse prognosis. See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of Oncology. 9th ed.* Philadelphia, Pa.: Lippincott Williams & Wilkins; 2011: 1368-1391.

The increased risk of developing ovarian cancer appears to be affected by several factors, including, but not limited to: (i) older women, and in those who have a first or second degree relative with the disease; (ii) hereditary forms of ovarian cancer can be caused by mutations in specific genes (most notably BRCA1, BRCA2, and genes for hereditary non-polyposis colorectal cancer); (iii) infertile women; (iv) women with endometriosis; and (v) women who have used or currently use postmenopausal estrogen replacement therapy.

Combination oral contraceptive pills have been shown to provide a protective factor for ovarian cancer. See, e.g., Bandera, C A. Advances in the understanding of risk factors for ovarian cancer. *J Reprod Med* 50(6):399-406 (2005). The relationship between use of oral contraceptives and ovarian cancer was shown in a summary of results of 45 case-control and prospective studies. Cumulatively these studies show a protective effect for ovarian cancers. Women who used oral contraceptives for 10 years had about a 60% reduction in risk of ovarian cancer. (a risk ratio 0.42 with statistically significant confidence intervals given the large study size). This was, by far, the largest epidemiological study to date on the subject (45 studies, over 20,000 women with ovarian cancer and about 80,000 controls). See, e.g., Collaborative Group on Epidemiological Studies of Ovarian Cancer, Beral V, Doll R, Hermon C, Peto R, Reeves G. Ovarian cancer and oral contraceptives: collaborative reanalysis of data from 45 epidemiological studies including 23,257 women with ovarian cancer and 87,303 controls. *Lancet* 371:(9609):303-314 (2008).

The link to the use of fertility medications (e.g., Clomiphene citrate) has been controversial. An analysis in 1991 raised the possibility that use of fertility drugs may increase the risk of ovarian cancer. However, several cohort studies and case-control studies have been subsequently conducted without demonstrating conclusive evidence for such a link. Thus, it will remain a complex topic to study as the infertile population differs in parity from the "normal" population. See, Id.

Early age at first pregnancy, older age of final pregnancy, and the use of low dose hormonal contraception have also been shown to have a protective effect. The risk is also lower in women who have had their fallopian tubes blocked surgically (tubal ligation). See, e.g., Bandera C A. Advances in the understanding of risk factors for ovarian cancer. *J. Reprod. Med.* 50(6): 399-406 (2005). Tentative evidence suggests that breastfeeding lowers the risk of developing ovarian cancer. See, e.g., Hunn, J; Rodriguez, G C. Ovarian cancer: etiology, risk factors, and epidemiology. *Clin. Obstet. Gynecol.* 55(1): 3-23 (2012).

II. The CA-125 Tumor Marker

CA-125 (cancer antigen 125) or Mucin 16 (MUC 16) is a protein that, in humans, is encoded by the MUC 16 gene. See, e.g., Yin B W, Dnistrian A, Lloyd K O. Ovarian cancer antigen CA125 is encoded by the MUC16 mucin gene. *Int. J. Cancer* 98(5):737-70 (2002). MUC 16 is a member of the mucin family glycoproteins. CA-125 has been identified as a tumor maker or biomarker whose levels may be elevated in the blood sera of some patients with specific types of cancers.

Mucin 16 is a membrane associated mucin that possesses a single transmembrane domain and contains 22,000 amino acid residues, making it the largest membrane associated mucin protein. MUC 16 is made of three different domains; an N-terminal domain, a tandem repeat domain, and a C-terminal. The N-terminal domain and tandem repeat domain are both entirely extracellular and are highly O-glycosylated. The tandem repeat domain has repeating sequences high in serine, threonine, and proline residues. The C-terminal domain contains multiple extracellular SEA (sea urchin sperm protein, enterokinase, and agrin) modules, a transmembrane domain, and a cytoplasmic tail. The extracellular region of MUC 16 can be released from the cell surface by undergoing proteolytic cleavage at a site thought to be located in the SEA modules.

CA-125 is the most frequently used biomarker for ovarian cancer detection. See, e.g., Suh K S, Park S W, Castro A, Patel H, Blake P, Liang M, Goy A. Ovarian cancer biomarkers for molecular biosensors and translational medicine. *Expert Rev. Mol. Diagnostics.* 10(8):1069-1083 (2010). Approximately 90% of women with advanced ovarian cancer have been shown to possess elevated levels of CA-125 in their blood serum, making CA-125 a useful tool for detecting ovarian cancer after the onset of symptoms. See, Id. Monitoring CA-125 blood serum levels is also useful for determining how ovarian cancer is responding to treatment (with the duration of disease-free survival correlating with the rate of fall of CA-125) and for predicting a patient's prognosis following treatment. See, e.g., Santillan A, Garg R, Zahurak M L, Gardner G J, Giuntoli R L, Armstrong D K, Bristow R E. Risk of epithelial ovarian cancer recurrence in patients with rising serum CA-125 levels within the normal range. *J. Clin. Oncol.* 23(36):9338-9343 (2005). In contrast, the persistence of high levels of CA-125 during therapy is associated with poor survival rates in patients. See, Id. Similarly, an increase in CA-125 levels within individuals in remission is a strong predictor of the recurrence of ovarian cancer. See, e.g., Santillan A, Garg R, Zahurak M L, Gardner G J, Giuntoli R L, Armstrong D K, Bristow R E. Risk of epithelial ovarian cancer recurrence in patients with rising serum CA-125 levels within the normal range. *J. Clin. Oncol.* 23(36):9338-9343 (2005). Moreover, rising CA-125 levels may precede clinical evidence of disease relapse by an interval of 3 to 6 months.

Prognosis relates to both the initial and post-treatment CA-125 values. A pre-operative value >65 U/mL suggests a poor prognosis. Persistent elevations following chemotherapy indicate a poor prognosis. The half-life of CA-125 after chemotherapy correlates with prognosis (patients with CA-125 half-life <20 days show improved survival). Time-to-normalization (rate of fall of CA-125) affects prognosis with more rapid normalization within 3 cycles of chemotherapy correlating with improved survival. See, Mais D D, Leonard G R (2009). *Quick Compendium Companion for Clinical Pathology* (2nd ed.). Chicago: American Society for Clinical Pathology. p. 352.

In April 2011 the UK's National Institute for Health and Clinical Excellence (NICE) recommended that women with symptoms that could be caused by ovarian cancer should be offered a CA-125 blood test. The aim of this guideline is to help diagnose the disease at an earlier stage, when treatment is more likely to be successful. Women with higher levels of the marker in their blood would then be offered an ultrasound scan to determine whether they need further tests.

The potential role of CA-125 for the early detection of ovarian cancer is controversial and has not yet been adopted for widespread screening efforts in asymptomatic women. The major issues with using the CA-125 biomarker are its lack of sensitivity, particularly for detecting early stages of ovarian cancer, and its lack of specificity, especially in premenopausal women. See, e.g., Nossov V, Amneus M, Su F, Lang J, Janco J M, Reddy S T, Farias-Eisner R. The early detection of ovarian cancer: from traditional methods to proteomics. Can we really do better than serum CA-125?. *Am. J. Obstet. Gynecol.* 199(3):215-223 (2008). These limitations mean that CA-125 testing often gives false positives for ovarian cancer and puts patients through unnecessary further screening (sometimes including surgery) and anxiety. Also, these limitations mean that many women with early stage ovarian cancer will receive a false negative from CA-125 testing and not get further treatment for their condition.

Wang, et al. showed a male patient with IgE myeloma possessed elevated level of serum CA125. See, Man-ling Wang, Qiang Huang, and Tian-xin Yang. IgE myeloma with elevated level of serum CA125. *J. Zhejiang. Univ. Sci. B.* 10(7):559-562 (2009).

CA-125 has limited specificity for ovarian cancer because elevated CA-125 levels can be found in individuals without ovarian cancer. For example, while CA-125 is best known as a marker for ovarian cancer, it may also be elevated in other cancers, including endometrial, fallopian tube, lung, breast, and gastrointestinal cancers. See, e.g., Bast R C, Xu F J, Yu Y H, Barnhill S, Zhang Z, Mills G B. CA 125: the past and the future. *Int. J. Biol. Markers* 13(4):179-187 (1998). CA-125 may also be elevated in a number of relatively benign conditions, such as endometriosis, several diseases of the ovary, menstruation, and pregnancy. It also tends to be elevated in the presence of any inflammatory condition in the abdominal area, both cancerous and benign. Thus, CA-125 testing is not perfectly specific for ovarian cancer and often results in false positives. The specificity of CA-125 is particularly low in premenopausal women because many benign conditions that cause fluctuations in CA-125 levels, such as menstruation, pregnancy, and pelvic inflammatory disease (PID), are seen in this population. Elevations in CA-125 can also be seen in cirrhosis and diabetes mellitus.

CA-125 testing is also not perfectly sensitive for detecting ovarian cancer because not every patient with cancer will have elevated levels of CA-125 in their blood. For example, 79% of all ovarian cancers are positive for CA-125, whereas the remainder do not express this antigen at all. See, e.g., Rosen D G, Wang L, Atkinson J N, Yu Y, Lu K H, Diamandis E P, Hellstrom I, Mok S C, Liu J, Bast R C. Potential markers that complement expression of CA125 in epithelial ovarian cancer. *Gynecol. Oncol.* 99(2):267-277 (2005). Also, only about 50% of patients with early stage ovarian cancer have elevated CA-125 levels. Since many patients with early stage ovarian cancer do not have elevated levels of CA-125, this biomarker has poor sensitivity for ovarian cancer, especially before the onset of symptoms.

While this test is not generally regarded as useful for large scale screening by the medical community, a high value may be an indication that the woman should receive further diagnostic screening or treatment. Normal values range from 0 to 35 U/mL. See, e.g., Nossov V, Amneus M, Su F, Lang J, Janco J M, Reddy S T, Farias-Eisner R. The early detection of ovarian cancer: from traditional methods to proteomics. Can we really do better than serum CA-125? *Am. J. Obstet. Gynecol.* 199(3):215-223 (2008). Elevated levels in post-menopausal women are usually an indication that further screening is necessary. In pre-menopausal women, the test is less reliable as values are often elevated due to a number of non-cancerous causes, and a value above 35 is not necessarily a cause for concern.

In a patient who is clinically selected for testing due to the presence of an adnexal/pelvic mass, CA-125 has great utility to differentiate benign from malignant processes. In a post-menopausal woman with a palpable adnexal mass and CA-125 level greater than 65 U/mL, the positive predictive value is >95% for ovarian malignancy. In patients who are not as carefully selected clinically, the utility of this test decreases, thus highlighting the need for careful clinical scrutiny.

MUC 16 has been shown to play a role in advancing tumorigenesis and tumor proliferation by several different mechanisms. One mechanism by which MUC 16 aids in the growth of tumors is by suppressing the response of Natural Killer Cells, thus protecting cancer cells from the immune response. See, e.g., Patankar M S, Jing Y, Morrison J C, Belisle J A, Lattanzio F A, Deng Y, Wong N K, Morris H R, Dell A, Clark G F. Potent suppression of natural killer cell response mediated by the ovarian tumor marker CA125. *Gynecol. Oncol.* 99(3):704-713 (2005). Further evidence of the role of MUC 16 in allowing tumor cells to evade the immune system is the discovery that the heavily glycosylated tandem replete domain of MUC 16 can bind galectin-1, an immunosuppressive protein.

MUC 16 is also thought to participate in cell-to-cell interactions that allow for the metastasis of tumor cells. This is supported by evidence showing that MUC 16 binds selectively to mesothelin, a glycoprotein normally expressed by the mesothelial cells of the peritoneum. MUC 16 and mesothelin interactions are thought to provide the first step in tumor cell invasion of the peritoneum. See, e.g., Rump A, Morikawa Y, Tanaka M, Minami S, Umesaki N, Takeuchi M, Miyajima A. Binding of ovarian cancer antigen CA125/MUC16 to mesothelin mediates cell adhesion. *J. Biol. Chem.* 279(10):9190-9198 (2005). Mesothelin has also been found to be expressed in several types of cancers including mesothelioma, ovarian cancer and squamous cell carcinoma. Since mesothelin is expressed by tumor cells, MUC 16 and mesothelial interactions may aid in the gathering of other tumor cells to the location of a metastasis, thus increasing the size of the metastasis. See, Id.

Evidence suggests that the cytoplasmic tail of MUC 16 enables tumor cells to grow and become motile and invasive. This appears to be due to the ability of the C-terminal domain of MUC 16 to decrease the expression of E-cadherin and increase the expression of N-cadherin and vimentin, which are expression patterns consistent with epithelial-mesenchymal transition. See, e.g., Thériault C, Pinard M, Comamala M, Migneault M, Beaudin J, Matte I, Boivin M, PichéA, Rancourt C. MUC16 (CA125) regulates epithelial ovarian cancer cell growth, tumorigenesis and metastasis. *Gynecol. Oncol.* 121(3):434-443 (2011).

MUC 16 may also play a role in reducing the sensitivity of ovarian cancer tumor cells to drug therapy. Overexpression of MUC 16 has been shown to protect cells from the effects of genotoxic drugs, such as cisplatin. See, e.g., Boivin M, Lane D, Piché A, Rancourt C. CA125 (MUC 16) tumor antigen selectively modulates the sensitivity of ovarian cancer cells to genotoxic drug-induced apoptosis. *Gynecol. Oncol.* 115(3):407-413 (2009).

III. Current Treatment Options for Advanced Epithelial Ovarian Cancer

As the probability for cure for patients with advanced ovarian cancer had previously been thought to be remote, with palliation and optimizing the quality of life being the primary treatment goals (see, e.g., Gordon A N, Fleagle J T, Guthrie D, Parkin D E, Gore M E, Lacave A J. Recurrent epithelial ovarian carcinoma: a randomized phase III study of pegylated liposomal doxorubicin versus topotecan. *J. Clin. Oncol.* 19(14):3312-3322 (2001)), the unexpected observations in the Phase III clinical trial disclosed in the present patent application regarding the ability of the subjects receiving Karenitecin to tolerate: (i) the full chemotherapeutic cycle regimen with reduced adverse effects and (ii) a greater number of total chemotherapeutic cycles, may serve to markedly improve the probability of advanced ovarian cancer being able to be treated as a chronic disease, or even for a cure.

The existing recommended treatment strategy for patients with advanced-stage ovarian cancer (stage III/IV) includes cytoreductive surgery (i.e., removal of all visible tumor) followed by platinum- and/or taxane-based chemotherapy. See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of Oncology.* 9th ed. Philadelphia, Pa.: Lippincott Williams & Wilkins; 2011:1368-1391. While almost 80% of previously-untreated patients with advanced stage disease achieve a complete clinical remission (CR) after platinum and taxane chemotherapy; between 50% and 75% of patients with advanced-stage disease ultimately experience relapse. Even patients who are surgically-confirmed to be in complete remission still remain at high-risk, with a relapse rate of 30% to 50% after platinum-based chemotherapy. See, Id.

The treatment strategy for patients with recurrent ovarian cancer is based upon the initial chemotherapy regimen used and on the initial response to treatment. Patients who respond to a platinum-based chemotherapy regimen and then experience a relapse after a disease-free interval of more than 6 months are considered platinum-sensitive (i.e., having a likelihood of achieving a secondary response, wherein said likelihood increases as the duration of disease-free interval increases); and are retreated with a platinum-based chemotherapy regimen. A single-agent carboplatin regimen is the currently preferred platinum compound for treatment of such platinum-sensitive recurrent disease. See, Id.

Although platinum-sensitive patients are frequently considered as candidates for re-treatment with regimens similar to those received in the first-line setting, there is no evidence from prospective, randomized trials that combination multi-agent chemotherapeutic regimens achieve superior outcomes in terms of survival or quality of life compared to the use of sequential single agents. In addition, early re-treatment with platinum places the patient at risk for cumulative hematologic and non-hematologic toxicity that can limit further therapy and diminish the overall quality of life. Most patients, however, eventually develop platinum-resistance, and salvage chemotherapy is much less effective than first-line chemotherapy. See, e.g., Piccart M J, Green J A, Lacave A J, et al. Oxaliplatin or paclitaxel in patients with platinum pretreated advanced ovarian cancer: a randomized phase II study of the European Organization for Research and Treatment of Cancer Gynecology Group. *J Clin Oncol.* 2000; 18(6):1193-1202. In some patients, the use of a non-platinum regimen may extend the platinum-free interval with less risk of cumulative toxicity. See, e.g., Markman M, & Bookman M A. Second-line treatment of ovarian cancer. *The Oncologist.* 2000; 5:26-35.

In contrast, those patients who do not respond to a platinum- and/or taxane-based chemotherapy regimen or who relapse within 6 months after completing a platinum- and/or taxane-based chemotherapy regimen are considered to be refractory or resistant to platinum and/or taxane drugs; and are generally not re-treated with these chemotherapy regimens. Chemotherapeutic drugs that have been shown to have some activity in patients with platinum- and/or taxane-resistant ovarian cancer include Topotecan, oral etoposide, gemcitabine, liposomal doxorubicin, vinorelbine, and altretamine. See, e.g., Karlan B Y, Markman M A, Eifel P J. Ovarian cancer, peritoneal carcinoma, and fallopian tube carcinoma. In: DeVita V T Jr, Hellman S, Rosenberg S A, eds. *Cancer. Principles & Practice of Oncology.* 9th ed. Philadelphia, Pa.: Lippincott Williams & Wilkins; 2011: 1368-1391. A total of four (4) drugs are currently approved by the United States Food and Drug Administration (FDA) for the treatment of recurrent ovarian cancer: (i) Taxol (paclitaxel, Bristol-Myers Squibb Company); (ii) Hycamtin (topotecan, GlaxoSmithKline); (iii) Doxil (doxorubicin HCl liposomal, Janssen); and (iv) Gemzar (gemcitabine, Eli Lilly) administered in combination with carboplatin.

Doxorubicin liposomal-formulation (Doxil) is an anthracycline antibiotic, closely related to the natural product daunomycin. Like all anthracyclines, it works by intercalating DNA. The drug is administered intravenously, as the hydrochloride salt. It may also be sold under the brand names Adriamycin PFS, Adriamycin RDF, or Rubex. Doxil is typically administered once a month at a dose of 50 mg/m² of body surface area, at a rate of approximately 1 mg/min. The most serious adverse effect of doxorubicin administration is life-threatening heart damage and/or heart conditions (e.g., congestive heart failure, cardiac arrhythmias, and the like). See, e.g., Sneader, Walter (2005). *Drug Discovery: A History.* New York: Wiley. p. 467.

Gemcitabine (Gemzar) is a nucleoside analog in which the hydrogen atoms on the 2' carbon of deoxycytidine are replaced by fluorine. As with fluorouracil and other analogues of pyrimidines, the triphosphate analogue of gemcitabine replaces one of the nucleic acid building blocks, in this case cytidine, during DNA replication. This replacement process arrests tumor growth, as only one additional nucleoside can be attached to the "faulty" nucleoside, resulting in cellular apoptosis. Another target of gemcitabine is the enzyme ribonucleotide reductase (RNR). The diphosphate analogue binds to RNR active site and irreversibly inactivates the enzyme. Once RNR is inhibited, the cell cannot produce the deoxyribonucleotides required for DNA replication and repair; thus cellular apoptosis is induced. Gemcitabine is administered by the intravenous route, as it is extensively metabolized by the gastrointestinal tract. Doses range from 1-1.2 g/m² of body surface area, according to type of cancer treated. The most commonly reported serious adverse effects were hematologic in nature, with neutropenia occurring in up to 90% of patients. See, e.g., Sneader, Walter (2005). *Drug Discovery: A History.* New York: Wiley. p. 259.

The camptothecin, Topotecan, is a treatment option for patients with advanced epithelial ovarian cancer. See, e.g., Herzog T J. Update on the role of Topotecan in the treatment of recurrent ovarian cancer. *The Oncologist.* 7:3-10 (2002). The principal toxicity of Topotecan is myelosuppression, which may limit its use in platinum-resistant patients due to often incomplete bone marrow recovery following previous platinum treatment.

The silicon-containing HLCD, Karenitecin, was specifically developed to markedly improve key limitations of other camptothecins, which include limitations in the following areas: (i) safety; (ii) antitumor activity; (iii) potency; (iv) metabolism; (v) bioavailability; and (vi) sensitivity to multi-drug resistance proteins. Additionally, Karenitecin is at least 600-fold less water soluble than camptothecin. Karenitecin has demonstrated clinical activity that appears to be superior to that of Topotecan. Furthermore, the safety profile of Karenitecin suggests a reduced incidence of severe (NCI-CTCAE ≥grade 3) hematologic toxicity. This is of particular importance since an improved hematologic toxicity profile may reduce the need for frequent monitoring of bone marrow function and treatment interventions (e.g., treatment delays, dose reductions, red blood cell [RBC] transfusions, growth factor support, and the like), thus improving patient safety and compliance, as well as the overall clinical benefit.

Results from three Phase I studies indicate that Karenitecin can be safely administered to patients at the dose level of 1.0 mg/m²/day I.V. over a one hour period of time for 5 consecutive days in a 3-week treatment cycle. The principal and dose-limiting toxicity is non-cumulative, reversible myelosuppression. Any gastrointestinal toxicity is generally ≤grade 2 and is not dose-limiting.

In four Phase II studies, Karenitecin demonstrated a good safety profile and evidence of clinical activity in patients with metastatic melanoma, advanced ovarian and peritoneal cancer, malignant glioma, and advanced non-small cell lung cancer (NSCLC).

The Phase II study in patients with advanced ovarian cancer who had failed prior treatments demonstrated potential efficacy outcomes with Karenitecin as evidenced by prolonged Time to Progression (TTP) as compared with historical results reported with Topotecan.

It should be noted that the previously-performed studies and earlier-stage clinical trials were of importance in the determination and development of the actual chemotherapeutic drug regimen for the Phase III clinical trial disclosed herein. The data from the aforementioned clinical trials had to be collected and carefully analyzed by the Inventors of the present patent application in order to seek and obtain permission from the various regulatory agencies (i.e., the FDA) to engage in more advanced clinical studies (e.g., Phase II→Phase III) with increased complexity and substantially greater numbers of patients. Conducting the Phase III clinical trial was critical for the inventions disclosed in the instant patent application in order to allow the evaluation of Karenitecin in this specific and rigorously selected patient population with a larger number of patients in which detailed measurements of PFS, total number of patient treatment cycles, safety related events, and other important clinical observations could be made in a larger patient population. By way of non-limiting example, PFS was radiographically determined by an Independent Radiologic Committee (IRC). Additionally, highly specific and advanced methodologies were used to, e.g., initially select, diagnosis, and/or define the patient population of the instant Phase III clinical trial. As described herein, the patients selected for inclusion in the instant Phase III clinical trial were all refractory or resistant to a prior documented treatment of a platinum- and/or taxane-based chemotherapy regimen. In addition, the Karenitecin Phase III clinical trial disclosed herein was designed to allow patients to continue receiving the study treatment until such time as their disease progressed and was also designed to carefully monitor the clinical study treatment cycles.

IV. Discovery and Initial Development of Camptothecin

In the late 1950s, CPT was isolated from *Camptotheca acuminata*, a tree native to China, its chemical structure was characterized, and evidence of potent antitumor activity was documented. See, e.g., Wall, M. E., et al., Plant antitumor agents. I. The isolation and structure of camptothecin, a novel alkaloidal leukemia and tumor inhibitor from *Camptotheca acuminata. J. Am. Chem. Soc.* 88:3888-3890 (1966). Although the naturally-occurring CPTs possessed antitumor activity, product formulation and delivery were problematic due to poor water solubility. As a means to address the poor water solubility, the water-soluble sodium salt form (or carboxylate form) of CPT was used in early clinical trials.

The structure of this originally isolated camptothecin (CPT) is shown below:

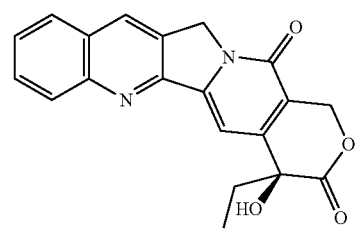

camptothecin (CPT)

These early clinical studies produced disappointing results in terms of both efficacy and safety by demonstrating substantially less antitumor activity than expected, and severe and unpredictable toxicity including hemorrhagic cystitis, diarrhea, and myelosuppression. See, e.g., Muggia, F. M., et al., Phase I clinical trial of weekly and daily treatment with camptothecin (NSC-100880): correlation with preclinical studies. *Cancer Chemother. Rep.* 56(4):515-521 (1972).

It was later discovered that an intact 20(S) lactone ring (i.e., lactone form) plays an essential role in the observed antitumor activity of CPTs; and that hydrolysis of the CPT lactone ring yields a carboxylate form of the molecule which has substantially lower antitumor activity. Because of its critical role in the antitumor activity of CPTs, the stability of the 20(S) lactone ring has been studied extensively in a variety of CPTs. See, e.g., Giovanella, B. C., et al., Dependence of anticancer activity of camptothecins on maintaining their lactone function. In: Liehr, J. G., Giovanella, B. C., and Verschraegen, C. F., eds. *The Camptothecins. Unfolding Their Anticancer Potential. Ann. New York Acad. Sci.* 922: 27-35 (2000).

V. Biochemical and Molecular Pharmacology of Camptothecins

A. Topoisomerase I

Topoisomerase I, the target enzyme of the camptothecins, is a 100 kDa protein composed of 765 amino acids. The enzymatic activity of topoisomerase I is found in a 67.7 kDa region located at the carboxyl-terminal end of the protein. The topoisomerase I gene is located on human chromosome 20, and it consists of 21 exons extending over 85 kilobases of DNA. Expression of topoisomerase I is found in nearly all mammalian cells at a high copy number, estimated at approximately $10^6$ per cell. See, e.g., Kunze, N., et al., The structure of the human type I DNA topoisomerase gene. *J. Biol. Chem.* 266:9610-9615 (1991).

Topoisomerase I acts to relax supercoiled double-stranded DNA, a function it partially shares with the related enzyme topoisomerase II. Unwinding of the DNA helix is essential for normal DNA function such as DNA replication or RNA transcription. This unwinding generates torsional strains in the DNA resulting from supercoiling of the helix above and below the region of ongoing nucleic acid synthesis. Topoisomerase I relaxes both positively- and negatively-supercoiled DNA and allows these functions to proceed in an orderly fashion. Although its exact role has not been fully elucidated, the involvement of topoisomerase I in RNA transcription has been postulated. High levels of topoisomerase I have been localized by immunohistochemical methods to regions of the nucleus that are active in RNA transcription, such as the nucleolus. See, e.g., Muller, M., et al., Eukaryotic type I topoisomerase is enriched in the nucleolus and catalytically active on ribosomal DNA. *EMBO J.* 4:1237 (1988). Although little is known about the regulation of topoisomerase I activity, phosphorylation by protein kinase C appears to activate the enzyme.

Unlike other topoisomerases, topoisomerase I is constitutively expressed at relatively constant levels throughout the cell cycle, even in cells that are actively dividing. Thus inhibitors of topoisomerase I, such as the camptothecins, may potentially be active in tumors that have low growth fractions and are resistant to other anticancer agents. In comparative studies, higher levels of topoisomerase I protein and mRNA were found in malignant colon and prostate tumors relative to their normal counterparts. See, e.g., Hussain, I, et al., Elevation of topoisomerase I messenger RNA, protein, and catalytic activity in human tumors. *Cancer Res.* 54:539 (1994). Consequently, the camptothecins may be selectively toxic to tumor cells compared with normal tissues.

B. Topoisomerase Molecular Function

Many of the steps involved in the topoisomerase I-mediated reaction that relaxes supercoiled DNA have been characterized at the molecular level. Topoisomerase I preferentially binds to supercoiled double-stranded DNA and cleaves the phosphodiester bond, resulting in a single-strand nick. During this process, the topoisomerase I enzyme is temporarily bound by a covalent bond between a tyrosine residue at position 723 and the 3'-terminus of the single-strand break in the DNA. This normally short-lived intermediate has been called the cleavable complex, and once it has been formed, free rotation of the DNA molecule can occur about the remaining intact phosphodiester bond, allowing for the relaxation of the torsional strain in the DNA. Finally, relegation of the strand break restores the integrity of the double-stranded DNA, and the enzyme dissociates from the now relaxed double helix. Typically, this reaction is very rapid, and topoisomerase I protein bound to DNA cannot be isolated under normal conditions.

C. Mechanism of Action of the Camptothecins

In the presence of camptothecins, the topoisomerase I enzymatic reaction is altered, resulting in a drug-induced stabilization of the cleavable complex. See, e.g., Potmesil, M., Camptothecins from bench research to hospital ward. *Cancer Res.* 54:1431 (1994). Camptothecins generally interact non-covalently with the DNA-bound topoisomerase I and inhibit the relegation step of the reaction. Consequently, there is accumulation of stabilized cleavable complexes and a persistence of single-stranded DNA breaks. However, this DNA damage alone is not toxic to the cell, because the lesions are highly reversible and can be repaired rapidly once the drug is removed. Instead, ongoing DNA synthesis is required in order to convert these stabilized cleavable complexes into more lethal DNA damage. See, e.g., D'Arpa, P., et al., Involvement of nucleic acid synthesis in cell killing mechanisms of topoisomerase poisons. *Cancer Res.* 50:6919 (1990). According to the "fork collision model," irreversible damage to the DNA occurs only when a DNA replication fork encounters a cleavable complex, resulting in the formation of a complete double-stranded break in the DNA. See, e.g., Tsao, Y. P., et al., Interaction between replication forks and topoisomerase I DNA cleavage complexes: studies in a cell-free SV-40 replication system. *Cancer Res.* 53:5908 (1993). Thus, the cleavable complexes are necessary, but not sufficient for drug toxicity. In support of this theory are observations that inhibitors of DNA synthesis, such as aphidicolin or hydroxyurea, can protect cells from camptothecin-induced cytotoxicity. If ongoing, DNA synthesis is truly necessary for drug-induced toxicity, then the camptothecins should be highly S-phase cell-cycle-specific in their action. This finding has been confirmed in most, but not all experimental studies. This point has important implications for the design of clinical therapeutic regimens, because highly S-phase-specific cytotoxic agents require prolonged exposures to drug concentrations above a minimum threshold in order to maximize the fractional cell kill.

Although the camptothecins can clearly produce irreversible DNA damage in the presence of ongoing DNA synthesis, the events responsible for cell death once these lesions occur have not been elucidated fully. The camptothecins, as well as other DNA-damaging agents, can cause cell-cycle arrest, typically in the $G_2$ phase. The molecular mechanisms responsible for regulation of this block in the cell cycle have been examined. Camptothecin-induced DNA damage correlates with altered activity of the p34$^{cdc2}$/cyclin B complex, which has been tightly linked to regulation of the $G_2$ to M-phase transition in the cell cycle. See, e.g., Tsao, Y. P., et al., Interaction between replication forks and topoisomerase I DNA cleavage complexes: studies in a cell-free SV-40 replication system. *Cancer Res.* 53:5908 (1993). The relevance of this $G_2$ block to cytotoxicity is not clear. Failure of cells to arrest at the $G_2$ checkpoint following drug treatment may be associated with increased camptothecin toxicity. A preliminary report suggests that the differential sensitivity of various cell lines to the camptothecins inversely correlates with their ability to undergo $G_2$ arrest following drug exposure. See, e.g., Goldwasser, F., et al., Integrity of $G_2$ checkpoint is a critical determinant for sensitivity to camptothecin. In: Programs and Abstracts. *The Fifth Conference on DNA Topoisomerases in Therapy*. New York, pg. 51 (1994). Other reported actions of the camptothecins include the induction of differential gene expression in human promonocytic leukemia cells, with the increased expression of the c-jun early-response gene. Finally, the camptothecins cytotoxicity also has been associated with the endonucleolytic degradation of DNA, resulting in a pattern of DNA fragmentation similar to that described for programmed cell death or apoptosis. Id. Further studies on the nature of cellular events that occur as a result of camptothecin-induced DNA damage are required.

Camptothecins also can damage DNA at the chromosomal level. Dose-dependent increases in sister chromatid exchange (SCE) and chromosomal aberrations were detected in the peripheral blood lymphocytes obtained from patients following irinotecan treatment. See, e.g., Kojima, A., et al., Cytogenetic effects of CPT-11 and its active metabolite, SN-38, on human lymphocytes. *Jpn. J. Clin. Oncol.* 23:116 (1993). The chromosomal damage was manifested mainly by chromatid gaps and breaks. Although little is known concerning the possible long-term side effects of camptothecin therapy, other DNA-damaging agents, such as alkylating agents, have been associated with mutagenicity. Additional study will be required to determine whether these risks are also relevant to the camptothecins.

The presence of topoisomerase I is essential for the generation of camptothecin-induced cytotoxicity. Mutant yeast cells that lack functional topoisomerase I are completely resistant to the camptothecins. However, when topoisomerase I is transfected into these mutants, drug sensitivity is restored. See, e.g., Nitiss, J. and Wang, J. C., DNA topoisomerase targeting antitumor drugs can be studied in yeast. *Proc. Natl. Acad. Sci. U.S.A.* 85:7501 (1988). These experiments illustrate how camptothecin's mechanism of action differs from the more traditional pharmacologic inhibition of an essential enzyme. In order to generate drug toxicity, complete inhibition of topoisomerase I is not necessary or even required. Instead, the camptothecins generate drug toxicity by converting a normally functioning constitutive protein, topoisomerase I, into a cellular poison.

D. Cleavage Site Sequence Specificity

Topoisomerase I cleavage is not a random event and the single-strand nicks appear with increased frequency at specific sequence sites in the DNA. See, e.g., Jaxel, C., et al., Effect of local DNA sequence on topoisomerase I cleavage in the presence or absence of camptothecin. *J. Biol. Chem.* 266:20418 (1991). Interestingly, camptothecin does not stabilize all topoisomerase I cleavable complexes equally. Instead, enhanced stabilization of cleavage sites by camptothecin occurs when a guanine residue is immediately 3' to the phosphodiester bond normally cleaved by the enzyme. In the absence of the drug, topoisomerase I has no specific base preference at this location, suggesting that only a subset of the total topoisomerase I cleavage sites is stabilized by camptothecin. This has led to a proposed camptothecin stacking model in which the drug specifically interacts with guanine residues at the topoisomerase I-DNA cleavage site. Preliminary findings also suggest that various camptothecin derivatives may stabilize different topoisomerase I cleavage sites. See, e.g., Tanizawa, A., et al., Comparison of topoisomerase I inhibition, DNA damage, and cytotoxicity of camptothecin derivatives presently in clinical trials. *J. Natl. Cancer Inst.* 86(11):836 (1994). An in-depth understanding of these site-specific interactions will be greatly facilitated by crystallographic characterization of the molecular structure of the camptothecin-stabilized cleavable complex.

E. Mechanisms of Camptothecin Drug Resistance

Although little is known about the mechanisms of camptothecin resistance in human tumors, in vitro camptothecin resistance has been characterized in several different cell lines. Single-base mutations in the topoisomerase I enzyme can decrease its interaction with the camptothecins, resulting in drug resistance. Recently, several different amino acid substitutions have been characterized in human topoisomerase I that confer a relative resistance to the camptothecins. These substitutions span a large portion of the protein, and they include changing a glycine 363 to cysteine, threonine 729 to alanine, and phenylalanine 301 to serine or aspartic acid 533 or 583 to glycine. See, e.g., The Camptothecins. In: *Cancer Chemotherapy and Biotherapy, 2$^{nd}$ Edition*. B. A. Chabner and D. L. Longo, eds. Lippincott-Raven Publishing New York, N.Y. (1996). Further research is likely to identify additional topoisomerase I mutants with relative camptothecin resistance. Insensitivity to the camptothecins also can result from decreased expression of topoisomerase I. In an in vitro study, a resistant subline of cells containing less than 4% of the topoisomerase I activity compared with wild-type parental cells was 1000-fold less sensitive to camptothecin. The decreased expression of topoisomerase I in this cell line was compensated for by a corresponding increase in topoisomerase II expression. Postulated mechanisms responsible for the decreased expression of topoisomerase I include chromosomal deletions or by permethylation of the topoisomerase I gene. See, e.g., Tan, K. B., et al., Nonproductive rearrangement of DNA topoisomerase I and II genes: correlation with resistance to topoisomerase inhibitors. *J. Natl. Cancer Inst.* 81:1732 (1994).

The role for the P-glycoprotein-associated multidrug resistance (MDR) phenotype in camptothecin resistance has not been clearly defined. In comparison studies, MDR-expressing sublines were nine-fold more resistant to Topotecan and two-fold more resistant to 9-aminocamptothecin than the parental wild-type cells. See, e.g., Chen, A. U., et al., Camptothecin overcomes MDR1-mediated resistance in human KB carcinoma cell lines. *Cancer Res.* 51:6039 (1991). No increase in resistance was observed for camptothecin or 10,11-methylenedioxycamptothecin. While other investigators have confirmed these observations, this degree of MDR-associated resistance is much less than the 200-fold change in sensitivity typically described for classic MDR substrates, such as doxorubicin or etoposide, in the same experiments. See, e.g., Mattern, M. R., et al., In vitro and in vivo effects of clinically important camptothecin analogues on multidrug-resistant cells. *Oncology Res.* 5:467 (1993). The relevance of these observations to the clinical setting requires further study.

Another potential mechanism for camptothecin resistance is decreased intracellular drug accumulation, which was observed in vitro. The biochemical processes responsible for these decreased intracellular drug levels have not been identified, and unfortunately, little is currently known about the mechanisms of camptothecin influx and efflux from cells. Finally, resistance to a camptothecin prodrug, such as irinotecan, may result from decreased intracellular production of the active metabolite SN-38 by the irinotecan converting-enzyme carboxylesterase. A preliminary association has been reported between the measured converting-enzyme activity in different tumor cell lines and their relative sensitivity to irinotecan. See, e.g., Chen, S. F., et al., Human tumor carboxylesterase activity correlates with CPT-11 cytotoxicity in vitro. *Proc. Am. Cancer Res.* 35:365 (1994).

The key biochemical or molecular determinants of tumor response to clinical camptothecin therapy have not yet been clearly identified. Because of the complex, stepwise pattern of drug-induced perturbations in cellular metabolism, it is possible that no single parameter will completely identify sensitive or resistant tumors. While the overall levels of topoisomerase I are important, other factors are also essential, including the degree of drug sensitivity of the topoisomerase I enzyme, the number of cleavable complexes stabilized, and the extent of ongoing DNA synthesis. Equally important, but even less understood, events that contribute to camptothecin cytotoxicity include DNA damage repair, the triggering of apoptosis, and alteration of the integrity of cell cycle control by, for example, $G_2$ checkpoint arrest. A detailed understanding of the relationship between each of these processes and camptothecin-induced cell death remains an important research goal.

F. Clinical Limitations of Currently-Available Camptothecin Analogues

An important limitation of currently-available camptothecins (CPTs), which contain the native 20(S) lactone E-ring, is that the lactone species (i.e., the biologically active moiety) persists in low concentrations (≤20%) of the total drug concentration) in human plasma at physiologic pH. It is well recognized that the lactone form of CPTs demonstrates substantially greater antitumor activity relative to the carboxylate form. The reported concentrations of the CPT lactone species are substantially higher in mice than in humans for CPT-11 and SN-38 (the active metabolite of CPT-11), 9-amino-camptothecin (9-$NH_2$-CPT, or 9-AC), 9-nitro-camptothecin (9-$NO_2$-CPT), and CPT. The low proportion and concentration of the lactone species of the CPTs in human plasma is thought to have a substantial effect in reducing the antitumor activity of CPTs containing the 20(S) lactone E-ring moiety.

In addition, the clinical utility of commercially available water-soluble CPTs may be limited by the following: reduced tissue diffusion and uptake, unfavorable variability in drug activation and/or metabolism, common clinical toxicities that can be dose-limiting, and susceptibility to tumor-mediated drug resistance mechanisms.

VI. Karenitecin

Highly lipophilic camptothecin derivatives (HLCDs), particularly those containing silicon-based moieties, are effective anti-cancer drugs. One of the most noted of the silicon-containing HLCDs is Karenitecin (also known as BNP1350; cositecan; IUPAC Nomenclature: (4S)-4-ethyl-4-hydroxy-11-[2-(trimethylsilyl)ethyl]-1H-pyrano[3':4':6,7]indolizino[1,2-b]quinoline-3,14(4H,12H)-dione, and also referred to as 7-(2'-trimethylsilyl)ethyl camptothecin)). Karenitecin has been tested in human clinical trials, ranging from Phase I to Phase III, in the United States and internationally. U.S. Pat. Nos. 5,910,491; 6,194,579; 7,687,487; 7,687,496; and 7,687,497; and U.S. patent application Ser. No. 13/068,244, filed May 6, 2011; Ser. No. 13/573,294, filed Sep. 7, 2012; and Ser. No. 13/694,255, filed Nov. 13, 2012, which are all incorporated by reference herein in their entirety, describe certain compositions, formulations, and processes for synthesizing Karenitecin and other related HLCDs.

The molecular structure of Karenitecin is shown in (A), below).

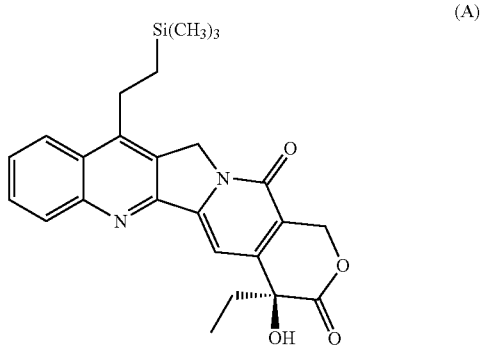

(A)

Karenitecin, and various analogs thereof, represent a novel class of chemotherapeutic compounds that have exhibited potent antineoplastic activity against common types of cancer including but not limited to cancers of the lung, breast, prostate, pancreas, head and neck, ovary, colon, as well as melanoma. While Karenitecin possesses Topoisomerase I inhibitory activity similar to that of other camptothecin derivatives, it also possess novel structural modifications that are rationally designed for superior bioavailability and tissue penetration, while concomitantly avoiding untoward metabolism and drug resistance mechanisms which are common in human and other mammalian cancers.

It may be ascertained from pharmacological and biochemical data, that many of the previously synthesized camptothecin analogs possess a number of inherent limitations which markedly decreases their usefulness as anticancer agents. In contrast, Karenitecin is a HLCD characterized by substantial lactone stability and long plasma half-life. In vitro studies conducted on a panel of over twenty (20) human cancer cell lines indicate that Karenitecin is a significantly more potent antitumor agent than either Topotecan or SN-38, the active metabolite of Irinotecan. Equilibrium dialysis studies with human plasma demonstrated that Karenitecin is 98 to 99% protein-bound. The free drug concentration in blood plasma is generally considered to be the pharmacologically active form in clinical pharmacology.

In addition, Karenitecin has significant utility as a highly efficacious chemotherapeutic drug, and it is significantly less toxic than previously disclosed camptothecin derivatives. Karenitecin also does not undergo A-ring or B-ring glucuronidation (and implicitly deglucuronidation). The lack of glucuronidation decreases deleterious physiological side-effects (e.g., diarrhea, leukopenia) and may also mitigate substantial interpatient variability in drug levels of the free metabolite and its glucuronide conjugate. Furthermore, Karenitecin is not a prodrug, thus it requires no metabolic activation.

Thus, in summation, Karenitecin: (i) possesses potent antitumor activity (i.e., in nanomolar or sub-nanomolar concentrations) for inhibiting the growth of human and animal tumor cells in vitro; (ii) is a potent inhibitor of Topoisomerase I; (iii) lacks susceptibility to MDR/MRP drug resistance; (iv) requires no metabolic drug activation; (v) lacks glucuronidation of the A-ring or B-ring; (vi) reduces drug-binding affinity to plasma proteins; (vii) maintains lactone stability; (viii) maintains drug potency; and (ix) possesses a low molecular weight (e.g., MW<600).

VII. Summary of Non-Clinical and Clinical Data with Karenitecin

Karenitecin is a novel, HLCD and is distinguished from other camptothecins on the basis of its highly novel chemical structure, possessing a tri-methyl silicon moiety. As previously discussed, some of the novel characteristics displayed by Karenitecin include, but are not limited to: (i) possesses potent antitumor activity (i.e., in nanomolar or sub-nanomolar concentrations) for inhibiting the growth of human and animal tumor cells in vitro; (ii) is a potent inhibitor of Topoisomerase I; (iii) lacks susceptibility to MDR/MRP drug resistance; (iv) requires no metabolic drug activation; (v) lacks glucuronidation of the A-ring or B-ring (which reduces inter-patient variability and gastrointestinal toxicity); (vi) reduces drug-binding affinity to plasma proteins; (vii) maintains lactone stability; (viii) maintains drug potency; and (ix) possesses a low molecular weight (e.g., MW<600). See, e.g., Yao, S., et al., Studies of the protein binding properties of Karenitecin (BNP1350), a novel highly lipophilic camptothecin analogue [abstract]. AACR Abstract 1786 (2003); Hausheer, F. H., et al., Karenitecins: new preclinical developments with BNP1350; a novel, potent highly lipophilic camptothecin [abstract]. AACR Abstract 741 (1999).

Karenitecin has a longer half-life in its active lactone form in plasma, when compared with reported half-lives of various other commercially-available camptothecins. Karenitecin also appears to be insensitive to all commonly-known tumor-mediated drug resistance mechanisms, including Breast Cancer Resistance Protein (BCRP), which is recognized to be a tumor-mediated drug resistance factor in human cancer for camptothecins. See, e.g., Maliepaard, M., et al., Circumvention of breast cancer resistance protein (BCRP)-mediated resistance to camptothecins in vitro using non-substrate drugs or the BCRP inhibitor GF120918. *Clin. Cancer Res.* 7:935-941 (2001).

Karenitecin has demonstrated significant anti-tumor activity in vitro and in vivo against various human xenograft tumor models for various tumor types including, but not limited to, human central nervous system (CNS), colon, melanoma, lung, breast, ovarian carcinoma, and glioblastoma multiform. See, e.g., Van Hattum, A. H., et al., Novel camptothecin derivative BNP1350 in experimental human ovarian cancer: determination of efficacy and possible mechanisms of resistance. *Int. J. Cancer.* 100:22-29 (2002); Keir, S. T., Hausheer, F. H., et al., Therapeutic activity of 7-[(2-trimethylsilyl)ethyl)]-20(s)-camptothecin against central nervous system tumor-derived xenografts in athymic mice. *Cancer Chemother. Pharmacol.* 48:83-87 (2001); Van Hattum, A. H., et al., New highly lipophilic camptothecin BNP1350 is an effective drug in experimental human cancer. *Int. J. Cancer* 88:260-266 (2000); Hausheer, F. H., et al., Karenitecins: further developments with BNP1350: a novel, highly lipophilic, lactone stable camptothecin [abstract]. AACR Abstract 1360 (2000).

The relative antitumor activity of Karenitecin in preclinical models is similar or superior to the antitumor activity observed with other camptothecins, and Karenitecin has demonstrated a high degree (e.g., approximately 85%) of lactone stability in humans.

Preclinical toxicology studies of Karenitecin administered intravenously as a single daily dose for five consecutive days in Fischer rats (bolus) and beagle dogs (one-hour infusion) demonstrated reversible myelosuppression (predominantly neutropenia), diarrhea, emesis and mucositis (canine) and mild to moderate, reversible (one-hour duration) hypersensitivity histamine release-related reactions (canine) A preclinical toxicology study of various doses of Karenitecin administered orally as single daily doses for five consecutive days in beagle dogs demonstrated a variety of toxicities including: anorexia; weight loss; gastrointestinal toxicity (manifested as diarrhea with hemorrhage); occasional vomiting; and myelosuppression (evidenced by neutropenia, thrombocytopenia, lymphopenia, and transient decreases in erythrocyte numbers). The Maximum Tolerated Dose (MTD) of orally administered Karenitecin was 0.075 mg/kg; approximately 2-times that of intravenous (I.V.) Karenitecin. In addition, a toxicology study of various single daily doses of Karenitecin administered orally and intravenously for five consecutive days showed good tolerability of oral doses. Toxicities were reversible and included: anorexia (seen in I.V. groups, but not oral groups); weight loss (high in I.V. groups, negligible in oral groups); infusional toxicities; gastrointestinal toxicities (diarrhea and vomiting); and myelosuppression (neutropenia, thrombocytopenia, and lymphopenia). Gastrointestinal toxicities were dose-dependent, and were more severe in the higher drug treatment groups. Oral gastrointestinal toxicities were delayed and mild compared with I.V.-associated toxicities. Other clinical observations included: infusional toxicities, excitement, hyperpnea, facial and pinnae edema, pruritis, forced bowel movements, vomiting, increased tearing, and ptyalism.

To date, there have been no serious hypersensitivity reactions reported by patients receiving Karenitecin. The dose-limiting toxicities (DLTs) of Karenitecin in humans, as determined in initial Phase I clinical studies, are reversible and non-cumulative neutropenia and thrombocytopenia.

Intravenous administration of Karenitecin has been evaluated in three Phase I clinical studies in patients with the following cancer types: (i) advanced solid tumors (adult patients) (see, e.g., Schilsky, R. L., Hausheer, F. H., et al., Phase I trial of Karenitecin administered intravenously daily for five consecutive days in patients with advanced solid tumors using accelerated dose titration [abstract]. ASCO Abstract 758 (2000)); (ii) refractory or recurrent solid tumors (pediatric patients); and (iii) recurrent malignant glioma (adult patients). Intravenous administration of Karenitecin has also been evaluated in four Phase 2 clinical studies in adult patients with the following cancer types: (i) primary malignant glioma; (ii) treatment of persistent or recurrent epithelial ovarian or primary peritoneal carcinoma in heavily pre-treated patients; (iii) malignant melanoma (see, e.g., Hausheer, F. H., et al., Phase II trial of Karenitecin (BNP1350) in malignant melanoma: clinical and translational study [abstract]. ASCO Abstract 7554 (2004); and (iv) relapsed or refractory non-small cell lung cancer (see, e.g., Miller, A. A., et al., MR for the Cancer and Leukemia Group B. Phase II trial of Karenitecin in patients with relapsed or refractory advanced non-small cell lung cancer (CALGB 30004) *Lung Cancer* 48:399-407 (2005)).

VIII. Phase III Karenitecin Clinical Study Design

It is important to note that if the results obtained from the previous pre-clinical studies and Phase I and Phase II clinical trials were dispositive, there would be no need to engage in the instant Phase III clinical trial; which is extremely expensive and time consuming. Conducting the Phase III clinical trial disclosed in the instant patent application was critical for the inventions disclosed in the present patent application in order to allow the evaluation of Karenitecin in this specific and rigorously selected patient population with a larger number of patients in which detailed measurements of PFS, total number of patients treated, safety related events, and other important clinical observations could be made in a larger patient population. Additionally, highly specific or more advanced methodologies were used to, e.g., initially select or diagnosis the patient population of the instant Phase III clinical trial. By way of non-limiting example, PFS was radiographically determined by an Independent Radiologic Committee (IRC).

Prior to the instant clinical trial, the primary treatment goals in patients with recurrent advanced ovarian cancer was improvement in quality of life and overall length of life; as these patients were generally regarded as not curable. Chemotherapy was administered to these patients as palliative treatment, and there is subjective evidence that chemotherapy can improve quality of life in these patients, but, as yet, there are no randomized studies performed which have compared chemotherapy to best supportive care. Accordingly, a new treatment in this setting that has similar or better efficacy and/or more tolerability would be potentially highly beneficial for this patient population.

The human clinical study disclosed in the present patent application was a multi-center, multi-national, randomized, open-label, active-controlled, Phase III clinical study to evaluate the safety and efficacy of Karenitecin compared with Topotecan; wherein the drugs were administered to each trial subject as a single, daily intravenous dose of either Karenitecin or Topotecan—[Karenitecin 1.0 mg/m$^2$/day×5 (first 5 consecutive days per cycle) in a 60 minute I.V. infusion or Topotecan 1.5 mg/m$^2$/day×5 (first 5 days consecutive days per cycle) in a 30 minute I.V. infusion] every 21 days in patients with stage III/IV advanced epithelial ovarian cancer who are resistant or refractory to platinum- and taxane-based chemotherapy regimens, as indicated by relapse/progression while currently on, or within 6 months of completion of, platinum/taxane treatment in a first-line or second-line setting. In addition, patients with a best response of stable disease (hereinafter "SD") after at least 6 cycles of platinum/taxane treatment in the first-line setting were considered platinum-resistant.

All patients admitted to this Phase III clinical trial were documented to be platinum- and/or taxane-resistant or refractory and have incurable disease. All patients admitted to the clinical study must have had their disease progress while receiving chemotherapeutic treatment or within 6 months of first or second line platinum/taxane-based treatment or to have had a best response of stable disease after of at least 6 cycles of platinum/taxane treatment in the first line setting. It is important to note that, currently, there is no FDA-approved chemotherapeutic drug for this specific aforementioned indication.

Approximately 80 study centers participated in this Phase III clinical study. The primary endpoint was Progression Free Survival (PFS), defined as the time period from the date of randomization to the date of first radiographically documented progressive disease or disease progression ("PD") or date of death due to any cause, taking the event date that occurs first.

Several chemotherapeutic agents are approved for use in patients who have failed initial treatment for advanced ovarian cancer. Most, if not all approved agents for the treatment of patients with advanced ovarian cancer are associated with significant toxicity, and therefore new agents need to be developed to assist in the achievement of the treatment goals. Topotecan has been approved by the FDA for the treatment of metastatic carcinoma of the ovary after failure of initial or subsequent chemotherapy. Topotecan has shown a trend to comparable or superior efficacy compared with both paclitaxel and Doxil in patients with platinum-resistant or refractory ovarian cancer. See, e.g., Gordon A N, Fleagle J T, Guthrie D, Parkin D E, Gore M E, Lacave A J. Recurrent epithelial ovarian carcinoma: a randomized phase III study of pegylated liposomal doxorubicin versus Topotecan. *J. Clin. Oncol.* 19(14):3312-3322 (1991); Ten Bokkel Huinink W, Gore M, Carmichael J, et al. Topotecan versus paclitaxel for the treatment of recurrent epithelial ovarian cancer. *J. Clin. Oncol.* 15(6):2183-2193 (1997).

The hallmark toxicity of Topotecan is myelosuppression, which may also compound bone marrow toxicity from prior platinum therapy, thus necessitating very careful monitoring of hemoglobin (Hgb) levels, platelet counts, and neutrophil counts; as well as treatment interventions that include treatment delays, dose reductions, growth factor support, and RBC transfusions. See, e.g., Armstrong D K, Spriggs D, Levin J, Poulin R, Lane S. Hematologic safety and tolerability of topotecan in recurrent ovarian cancer and small cell lung cancer: an integrated analysis. *Oncologist.* 10(9): 686-694 (2005).

The Primary and Secondary Endpoints of the Phase III clinical study disclosed herein were as follows:
Primary Endpoint:
The primary endpoint was Progression Free Survival (PFS); defined as the time period from the date of randomization to the date of first radiographically documented progressive disease (PD) or date of death due to any cause, taking the event date that occurs first. The date of PD was determined by radiographically objective disease (RECIST) measurement.
Secondary Endpoints:
  Overall Survival (OS), defined as the time from the date of randomization to the date of death due to any cause.
  Incidence of anemia, defined as the proportion of patients who experience ≥grade 3 anemia based on National Cancer Institute Common Terminology Criteria for Adverse Events (NCI-CTCAE) criteria at any time post-baseline after receiving study treatment.
  Incidence of neutropenia (including febrile neutropenia), defined as the proportion of patients who experience ≥grade 3 neutropenia based on NCI-CTCAE criteria at any time post-baseline after receiving study treatment.
  Incidence of thrombocytopenia, defined as the proportion of patients who experience ≥grade 3 thrombocytopenia based on NCI-CTCAE criteria at any time post-baseline after receiving study treatment.

Patients underwent procedures throughout four (4) defined periods in this study, which are briefly described below. Various clinical, laboratory, and disease evaluations were required for each of these for each periods.

Period I (Screening and Randomization): Patient eligibility was determined by compliance with protocol-specified inclusion and exclusion criteria. Patients who signed the informed consent, and successfully complete the screening process, including documentation of disease status by radiographic measures, were randomized to receive study treatment.

Period II (Active Treatment): During this period, patients received either Karenitecin (1.0 mg/m$^2$/day administered as a 60-minute intravenous infusion) or Topotecan (1.5 mg/m$^2$/day administered as a 30-minute intravenous infusion) daily for 5 consecutive days, every 21 days (one treatment cycle=21 days). Patients continued the study treatment until they met one of the criteria listed below:

Patients with PD discontinued study treatment, and progressed to Period III.

Patients with SD or partial response (PR) could continue study treatment provided that they (a) continued to have evidence of clinical benefit (either objective tumor response or the absence of PD), and (b) they did not experience unacceptable treatment-related toxicity that was deemed by the treating physician to endanger the safety of the patient if they were to continue study treatment.

Patients who experienced a documented (radiographic) complete response (CR) at any time would continue treatment for 2 cycles (approximately 6 additional weeks) following the initial documentation of CR, provided that the patient did not experience any unacceptable treatment-related toxicity.

After completion of the additional 2 cycles (6 weeks) of treatment, patients had repeat radiographic documentation of the extent of disease to confirm the CR. After confirmation (radiographic) of the CR, the patient has completed study treatment, and will progress to Period III.

Period III (End of Treatment): Within ±3 days of date of treatment discontinuation, end-of treatment procedures will be conducted during Period III. Tumor measurements and response assessments will only need to be completed during Period III if the regularly-scheduled tumor measurements/response assessments fall into the Period III time interval. Tumor measurements/response assessments were required to remain on the 6 week schedule. Radiographic scans, response assessments, and CA-125 levels continued to be collected as described in Period IV.

Period IV (Follow-Up for Progression and Survival): All patients were followed for progression and survival. All patients were assessed for best overall response at the time they reach PD or start any alternative therapy.

Follow-Up for Progression (Patients Discontinuing for Reasons Other than PD):

Patients who discontinue from the study for any reason other than PD must continue to undergo radiographic scans, response assessments, and CA-125 level assessments every 6 weeks (±5 days) until PD or until the initiation of new treatment, after which they will proceed to follow-up for survival.

Follow-Up for Survival (All Patients): Patients with documented PD were followed up for survival (and date of any alternative therapy) by telephone and/or letter confirmation every 3 months until death.

IX. Phase III Clinical Trials Results

Simultaneous statistical analyses were performed on the clinical trial data from the time points when 254 and 338 Progression Free Survival (PFS) events occurred during the aforementioned Karenitecin Phase III Trial and the following results were observed. Unless otherwise noted, reported data is based on all patient events available at the time of analysis.

A greater than 6 week median progression-free survival (PFS) advantage in favor of Karenitecin (as compared with Topotecan) in subjects having advanced epithelial ovarian cancer which exhibits evidence of being refractory or resistant to platinum/taxane-based chemotherapy (P-value=0.261; Hazard Ratio (HR)=0.885). Median PFS was approximately 24.3 weeks for the Karenitecin arm compared to 17.8 weeks for the Topotecan arm. The PFS for Karenitecin and Topotecan was determined using an Independent Radiologic Committee (IRC).

A 2 month median progression-free survival (PFS) advantage in favor of Karenitecin (as compared with Topotecan) was found in the "Histopathology class: Mucinous adenocarcinoma" subtype of trial subjects. The PFS benefit for Karenitecin in comparison to Topotecan was determined using an Independent Review Committee (IRC). Median PFS was approximately 17.8 weeks for the Karenitecin arm for this subtype compared to 9.1 weeks for the Topotecan arm for this subtype. In addition, an overall survival (OS) of 35 months was observed in the third quartile of the Karenitecin arm for the Mucinous adenocarcinoma ovarian cancer subtype as compared to an OS of 19.4 months for the third quartile of the Topotecan arm for this subtype. An improvement in the overall survival hazard ratio in favor of Karenitecin (as compared with Topotecan) was also observed in the "Histopathology class: Mucinous adenocarcinoma" subtype of trial subjects, resulting in an observed hazard ratio of 0.841, P-value 0.7321.

A median progression-free survival (PFS) of approximately 8.2 weeks in favor of Karenitecin (as compared with Topotecan) was found in the subpopulation of subjects who were either refractory or resistant to platinum- and/or taxane-based chemotherapy and/or had the mucinous adenocarcinoma sub-type of ovarian cancer (P-value=0.0849; HR=0.770 with the analysis of subjects based on the first 254 PFS events in the clinical trial). Median PFS was approximately 26.9 weeks for the Karenitecin arm for this subpopulation of patients compared to 18.7 weeks for the Topotecan arm for this subpopulation. The PFS benefit for Karenitecin in comparison to Topotecan was determined using an Independent Radiologic Committee (IRC).

A 3 month median progression-free survival (PFS) advantage in favor of Karenitecin (as compared with Topotecan) was found in the "Best response stable disease (SD) after 6 cycles in a first-line setting" sub-category of trial subjects (P-value=0.9908; HR=0.992). The PFS benefit for Karenitecin and Topotecan was determined using an Independent Radiologic Committee (IRC).

A 6.5 week median progression-free survival (PFS) advantage in favor of Karenitecin (as compared with Topotecan) was found in the "Ovary as primary site of disease" sub-category of trial subjects (P-value=0.2606; HR=0.885). The PFS benefit for Karenitecin in comparison to Topotecan was determined using an Independent Radiologic Committee (IRC).

A 4.2 month median progression-free survival (PFS) advantage in favor of Karenitecin (as compared with Topotecan) was found in the "FIGO Stage 111B" sub-category of trial subjects (P-value=0.6225; HR=0.722). The PFS benefit for Karenitecin in comparison to Topotecan was determined using an Independent Radiologic Committee (IRC).

A 2.7 month median progression-free survival (PFS) advantage in favor of Karenitecin (as compared with Topotecan) was found in the "FIGO Stage IV" sub-category of trial subjects (P-value=0.0556; HR=0.741). The PFS benefit for Karenitecin in comparison to Topotecan was determined using an Independent Radiologic Committee (IRC). An improvement in the overall survival hazard ratio in favor of Karenitecin (as compared with Topotecan) was also observed in the "FIGO Stage IV" subtype of trial subjects, resulting in an observed hazard ratio of 0.892, P-value 0.4516.

A 2.8 month median progression-free survival (PFS) advantage in favor of Karenitecin (as compared with Topotecan) was found in the "FIGO Stage IV" sub-category of trial subjects, with the analysis of subjects based on the first 254 PFS events in the clinical trial (P-value=0.0260; HR=0.669). The PFS benefit for Karenitecin in comparison to Topotecan was determined using an Independent Radiologic Committee (IRC).

A 2.5 month median progression-free survival (PFS) advantage in favor of Karenitecin (as compared with Topotecan) was found in the "Histological Stage: G2-moderately differentiated" sub-category of trial subjects (P-value=0.2982; HR=0.835). The PFS benefit for Karenitecin in comparison to Topotecan was determined using an Independent Radiologic Committee (IRC).

A 1.6 month median progression-free survival (PFS) advantage in favor of Karenitecin (as compared with Topotecan) was found in the "Histopathology class: serous adenocarcinoma" sub-category of trial subjects (P-value=0.2829; HR=0.873). The PFS benefit for Karenitecin in comparison to Topotecan was determined using an Independent Radiologic Committee (IRC).

A 2.7 month median progression-free survival (PFS) advantage in favor of Karenitecin (as compared with Topotecan) was found in the "Histopathology class: Adenocarcinoma (grade ≥2) not otherwise specified" sub-category of trial subjects (P-value=0.3700; HR=0.684). The PFS benefit for Karenitecin in comparison to Topotecan was determined using an Independent Radiologic Committee (IRC). An improvement in the overall survival hazard ratio in favor of Karenitecin (as compared with Topotecan) was also observed in the "Histopathology class: Adenocarcinoma (grade ≥2) not otherwise specified" subtype of trial subjects, resulting in an observed hazard ratio of 0.898, P-value 0.7893.

A 3.9 month median progression-free survival (PFS) advantage in favor of Karenitecin (as compared with Topotecan) was found in the "ECOG Performance Status 0" sub-category of trial subjects (P-value=0.0249; HR=0.662). The PFS benefit for Karenitecin in comparison to Topotecan was determined using an Independent Radiologic Committee (IRC).

A 1.5 month median progression-free survival (PFS) advantage in favor of Karenitecin (as compared with Topotecan) was found in the "ECOG Performance Status 2" sub-category of trial subjects (P-value=0.7481; HR=0.896). The PFS benefit for Karenitecin in comparison to Topotecan was determined using an Independent Radiologic Committee (IRC).

Consistent with the overall trial population, the median progression-free survival (PFS) advantage in favor of Karenitecin (as compared with Topotecan) was also observed to improve for the resistant subject subpopulation (P-value=0.144; HR=0.822).

A 1.7 week median progression-free survival (PFS) advantage in favor of Karenitecin (as compared with Topotecan) was found in the "Histological Stage: G1-well differentiated" sub-category of trial subjects (P-value=0.8561; HR=0.904). The PFS benefit for Karenitecin in comparison to Topotecan was determined using an Independent Radiologic Committee (IRC). An improvement in the overall survival hazard ratio in favor of Karenitecin (as compared with Topotecan) was also observed in the "Histological Stage: G1-well differentiated" subtype of trial subjects, resulting in an observed hazard ratio of 0.9612, P-value 0.974.

An improvement in the overall survival hazard ratio in favor of Karenitecin (as compared with Topotecan) was also observed in the "Histopathology Class: Undifferentiated carcinoma" subtype of trial subjects, resulting in an observed hazard ratio of 0.6426, P-value 0.701.

An increase in the median number of treatment cycles able to be given to patients was observed for Karenitecin compared to Topotecan in the Karenitecin Phase III Trial, with a median of 6.0 treatment cycles for the Karenitecin arm of the Karenitecin Phase III Trial compared to a median of 5.0 treatment cycles for the Topotecan arm of the Karenitecin Phase III Trial.

The Karenitecin arm also demonstrated important safety/toxicity advantages with respect to the reduction of anemia (P-value=0.049) and thrombocytopenia (P-value=0.073). Grade 3 or 4 anemia events were reduced by 27.3% in the Karenitecin arm of the Karenitecin Phase III Trial in comparison to the Topotecan arm of the Karenitecin Phase III Trial. Grade 3 or 4 thrombocytopenia events were reduced by 37.4% in the Karenitecin arm of the Karenitecin Phase III Trial in comparison to the Topotecan arm of the Karenitecin Phase III Trial. A reduction in grade 4 neutropenia for the Karenitecin arm of the Karenitecin Phase III Trial was observed as well, with grade 4 neutropenia reduced by 38.2% in the Karenitecin arm of the Karenitecin Phase III Trial in comparison to the Topotecan arm of the Karenitecin Phase III Trial. In addition, no safety concerns related to Karenitecin were noted during the entire duration of the instant Phase III clinical study as monitored by the independent Data and Safety Monitoring Board (DSMB), and there were also no reports of reportable safety events related to Karenitecin which occurred to the Inventor's knowledge.

All patents, publications, scientific articles, web sites, and the like, as well as other documents and materials referenced or mentioned herein are indicative of the levels of skill of those skilled in the art to which the present invention pertains, and each such referenced document and material is hereby incorporated by reference to the same extent as if it had been incorporated by reference in its entirety individually or set forth herein in its entirety. Applicant reserves the right to physically incorporate into this specification any and all materials and information from any such patents, publications, scientific articles, web sites, electronically available information, and other referenced materials or documents.

The written description portion of this patent includes all claims. Furthermore, all claims, including all original claims as well as all claims from any and all priority documents, are hereby incorporated by reference in their entirety into the written description portion of the specification, and Applicant reserves the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in the written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application(s) leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The present invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y". The letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicant reserves the right to revise the application or claims to refer specifically to any individual member or any subgroup of members of the Markush group.

Other embodiments are within the following claims. The patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicant(s).

What is claimed is:

1. A method for increasing the time period of Progression Free Survival (PFS) in a subject having the mucinous adenocarcinoma-subtype of ovarian cancer, where the subject's cancer is not sensitive to treatment with platinum and/or taxane cancer treating agents; wherein said method is comprised of the i.v. and/or oral administration of Karenitecin in an amount sufficient to provide a therapeutic benefit to said subject.

2. A method for increasing the time period of Progression Free Survival (PFS) while concomitantly reducing the occurrence and/or the grade of occurrence of chemotherapy-induced adverse effects in a subject having the mucinous adenocarcinoma-subtype of ovarian cancer and where the subject's cancer has previously failed to respond to treatment with a platinum and/or taxane cancer treating agent(s) for a time of 180 days or more, or whose tumor(s) relapsed or progressed within 180 days of completion of treatment with a platinum and/or taxane cancer treating agent(s); wherein said method is comprised of the i.v. and/or oral administration of Karenitecin in an amount sufficient to provide a therapeutic benefit to said subject.

3. The method of claim 1 or claim 2, wherein said method consists of the administration of Karenitecin in a dosage of 1.0 mg/m$^2$/day by a 60 minute i.v. infusion for the first 5 consecutive days of each treatment cycle, where each treatment cycle is comprised of 21 total days.

4. The method of claim 1 or claim 2, wherein the number of treatment cycles is at least 6 treatment cycles.

5. A method for second line, single agent treatment of a subject having the mucinous adenocarcinoma subtype of ovarian cancer and where the subject's cancer is not sensitive to treatment with platinum and/or taxane cancer treating agents; wherein said method is comprised of the i.v. and/or oral administration of Karenitecin in an amount sufficient to provide a therapeutic benefit to said subject.

6. A method for the treatment of a subject having advanced ovarian cancer that is resistant or not sensitive to treatment with platinum and/or taxane chemotherapeutic agents while concomitantly reducing the occurrence and/or the grade of occurrence of chemotherapy-induced adverse effects in said subject; wherein said method is comprised of the i.v. and/or oral administration of Karenitecin in an amount sufficient to provide a therapeutic benefit to the subject having advanced ovarian cancer, including the mucinous adenocarcinoma-subtype of ovarian cancer.

7. A method for increasing the overall survival (OS) while concomitantly reducing the occurrence and/or the grade of occurrence of chemotherapy-induced adverse effects in a subject having the mucinous adenocarcinoma-subtype of ovarian cancer and where the subject's cancer is resistant or not sensitive to treatment with platinum and/or taxane cancer treating agents; wherein said method is comprised of the i.v. and/or oral administration of Karenitecin in an amount sufficient to provide a therapeutic benefit to said subject.

* * * * *